United States Patent
Hermary et al.

(10) Patent No.: US 9,377,413 B2
(45) Date of Patent: Jun. 28, 2016

(54) ENHANCED IMAGING METHOD AND APPARATUS

(75) Inventors: Alexander Thomas Hermary, Belcarra (CA); Mohammad Reza Sahraei, North Vancouver (CA); Terrance John Hermary, Coquitlam (CA); Michael Douglas Ball, Kelowna (CA)

(73) Assignee: HERMARY OPTO ELECTRONICS INC., Coquitlam, BC (CA)

( * ) Notice: Subject to any disclaimer, the term of this patent is extended or adjusted under 35 U.S.C. 154(b) by 140 days.

(21) Appl. No.: 13/502,363

(22) PCT Filed: Jul. 2, 2010

(86) PCT No.: PCT/CA2010/000994
§ 371 (c)(1),
(2), (4) Date: Apr. 16, 2012

(87) PCT Pub. No.: WO2011/044660
PCT Pub. Date: Apr. 21, 2011

(65) Prior Publication Data
US 2012/0218437 A1    Aug. 30, 2012

(30) Foreign Application Priority Data
Oct. 17, 2009   (CA) .................................... 2683206

(51) Int. Cl.
| | | |
|---|---|---|
| *H04N 5/228* | (2006.01) | |
| *G01N 21/898* | (2006.01) | |
| *G01B 11/245* | (2006.01) | |
| *G01B 11/25* | (2006.01) | |
| *G06T 5/00* | (2006.01) | |

(52) U.S. Cl.
CPC .......... *G01N 21/8986* (2013.01); *G01B 11/245* (2013.01); *G01B 11/2545* (2013.01); *G06T 5/007* (2013.01); *G06T 2207/30161* (2013.01)

(58) Field of Classification Search
None
See application file for complete search history.

(56) References Cited

U.S. PATENT DOCUMENTS

| | | | | |
|---|---|---|---|---|
| 6,157,747 | A * | 12/2000 | Szeliski ................ | G06K 9/209 345/419 |
| 6,677,944 | B1 * | 1/2004 | Yamamoto ............. | G06T 17/00 345/422 |
| 2003/0160970 | A1 * | 8/2003 | Basu .................. | G01B 11/2518 356/601 |
| 2004/0227766 | A1 * | 11/2004 | Chou ..................... | G06T 15/04 345/582 |
| 2004/0246473 | A1 * | 12/2004 | Hermary ............. | G01B 11/245 356/237.1 |
| 2005/0129325 | A1 * | 6/2005 | Wu ............................. | 382/254 |
| 2006/0038901 | A1 * | 2/2006 | Tapes ......................... | 348/254 |
| 2008/0101688 | A1 * | 5/2008 | Quadling ........... | G01B 11/2527 382/154 |
| 2009/0040371 | A1 * | 2/2009 | Hunter ...................... | 348/425.1 |
| 2009/0123045 | A1 * | 5/2009 | Quadling ............... | G06T 15/04 382/128 |
| 2009/0322892 | A1 * | 12/2009 | Smith et al. ............... | 348/222.1 |

\* cited by examiner

*Primary Examiner* — Twyler Haskins
*Assistant Examiner* — Wesley J Chiu

(57) ABSTRACT

This invention provides accurate, high quality images for the identification of the surface characteristics of an object, that may be used as an input to suitable industrial process. It involves acquiring a first raw scan of a portion of a target object across a scan line in a scan zone with a first camera and simultaneously acquiring a second raw scan of the same portion of the target object across the scan line in the scan zone with a second camera. The raw scans are converted to digital and then processed with flattening coefficients derived from measurements of variations in illumination. The first and second cameras sets of flattened image data are then gridized to compensate for parallax, make them orthographic sets of image data that can be compared on a pixel-by-pixel basis with a known or measured geometric profile of the target. A selection of enhanced pixel value for a surface coordinate can then be made, based on both sets of data. The obscuring of surface features by specular reflection can thus be effectively eliminated.

40 Claims, 30 Drawing Sheets

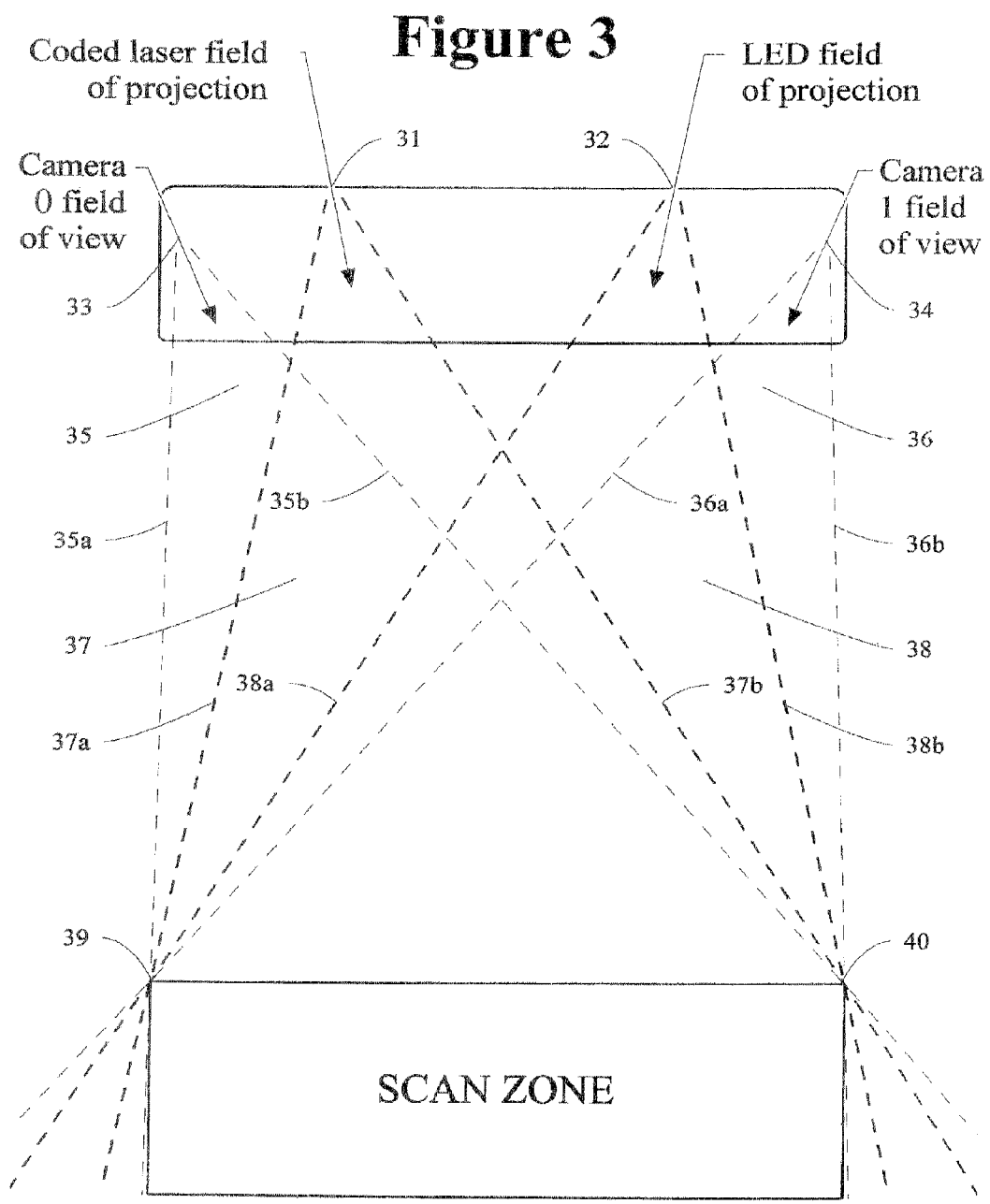

Specular

Diffuse

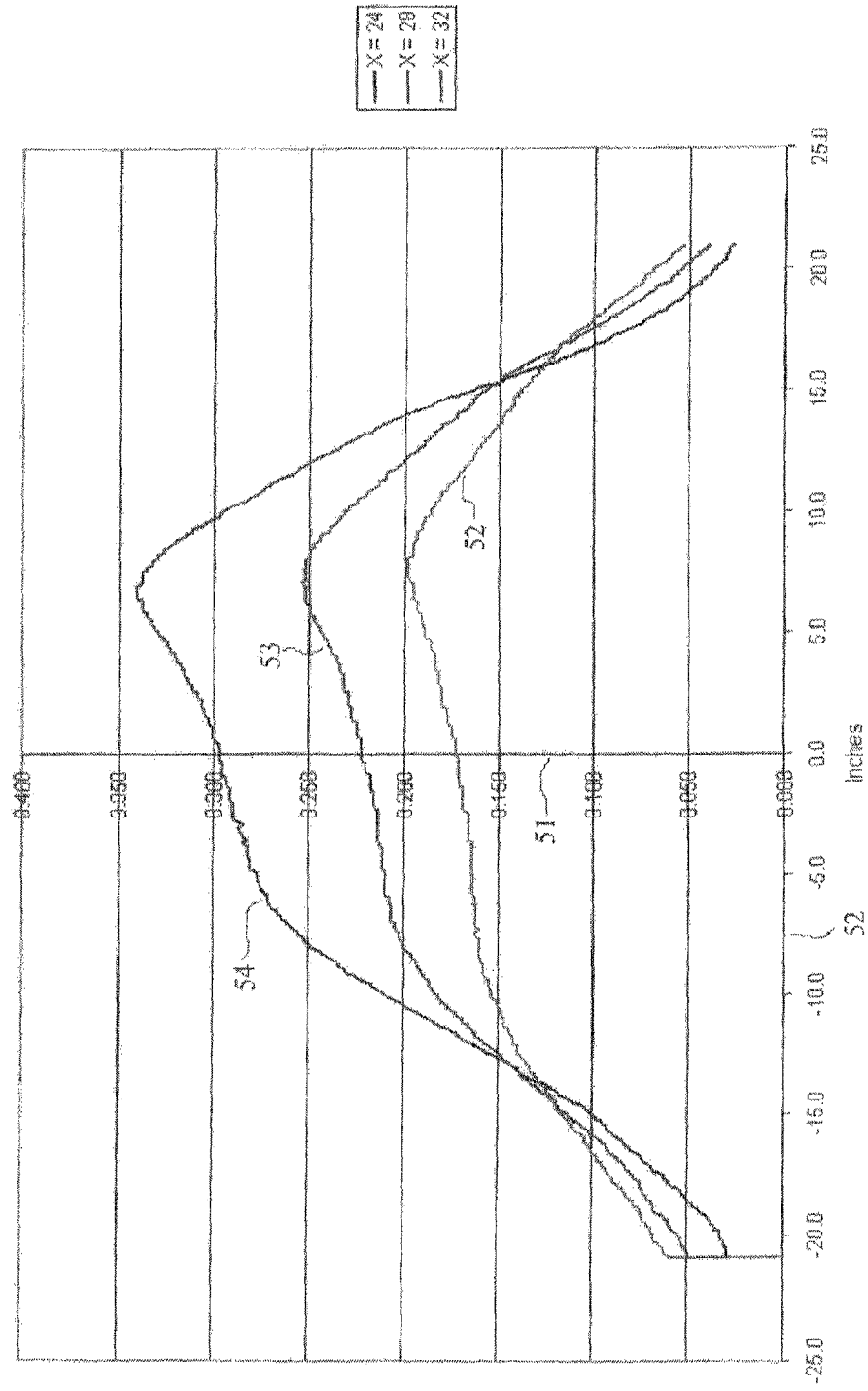

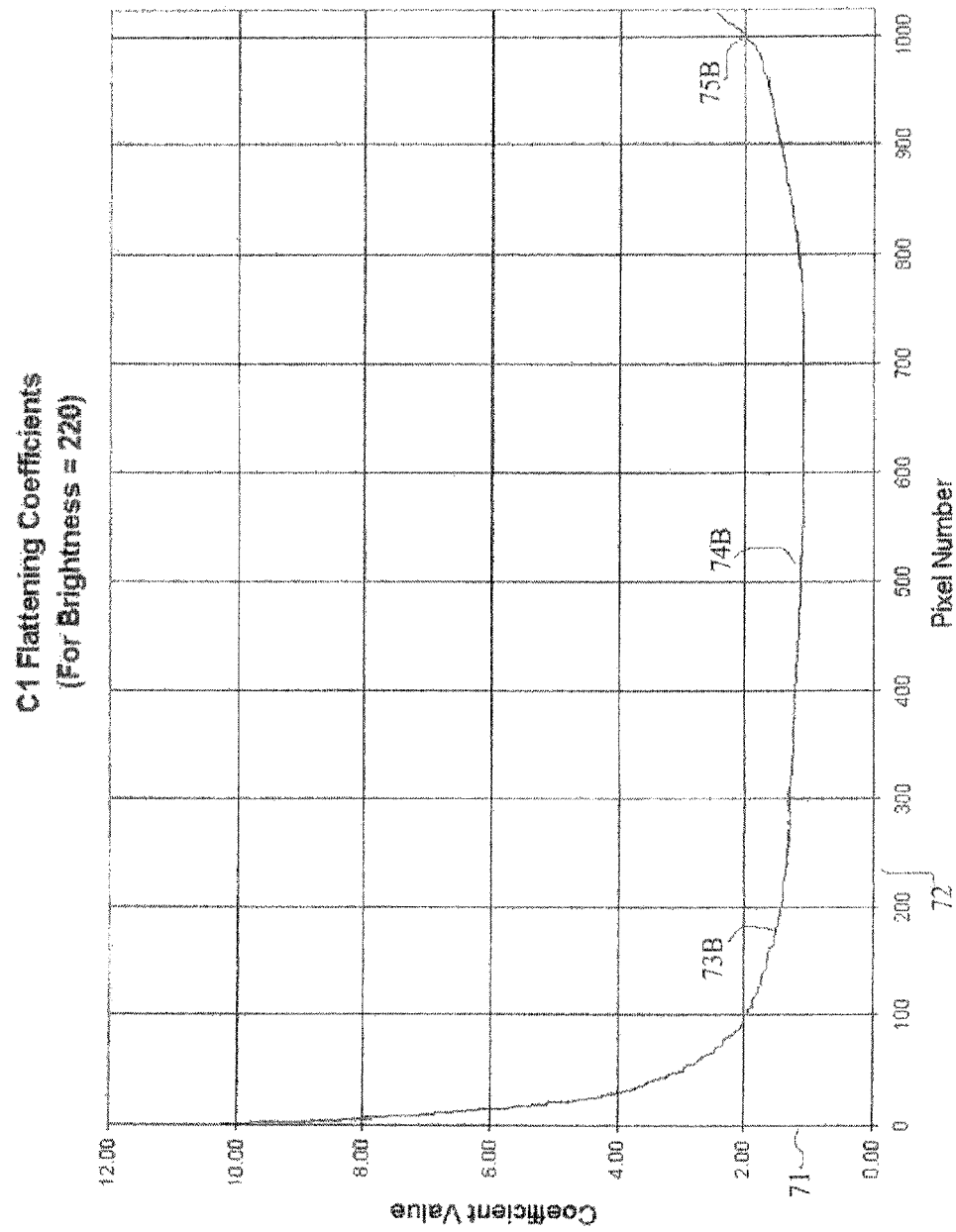

Figure 9

| | C1 GrayCard | | | | | | | |
|---|---|---|---|---|---|---|---|---|
| | Raw Data 1 | | Flattening Coefficient | | Flattened GrayCard Bright Lvl 220 | | Ortho GrayCard | |
| Range | 24 | | 24 | | 24 | | 24 | |
| Pixel | X = 24 | Pixel | X = 24 | Pixel | X = 24 | Pixel | X = 24 |
| 0 | 21 | 0 | 10.48 | 0 | 220.00 | 0 | 190 |
| 1 | 22 | 1 | 10.00 | 1 | 220.00 | 1 | 190 |
| 2 | 23 | 2 | 9.57 | 2 | 220.00 | 2 | 190 |
| 3 | 25 | 3 | 8.80 | 3 | 220.00 | 3 | 190 |
| 4 | 25 | 4 | 8.80 | 4 | 220.00 | 4 | 190 |
| 5 | 28 | 5 | 7.86 | 5 | 220.00 | 5 | 190 |
| 6 | 27 | 6 | 8.15 | 6 | 220.00 | 6 | 190 |
| 7 | 28 | 7 | 7.86 | 7 | 220.00 | 7 | 190 |
| 8 | 30 | 8 | 7.33 | 8 | 220.00 | 8 | 190 |
| 9 | 32 | 9 | 6.88 | 9 | 220.00 | 9 | 190 |
| 10 | 31 | 10 | 7.10 | 10 | 220.00 | 10 | 190 |
| 11 | 33 | 11 | 6.67 | 11 | 220.00 | 11 | 190 |
| 12 | 35 | 12 | 6.47 | 12 | 226.47 | 12 | 190 |
| 13 | 34 | 13 | 6.29 | 13 | 213.71 | 13 | 190 |
| 14 | 36 | 14 | 6.11 | 14 | 220.00 | 14 | 190 |
| 15 | 38 | 15 | 5.79 | 15 | 220.00 | 15 | 190 |
| 16 | 39 | 16 | 5.64 | 16 | 220.00 | 16 | 190 |
| 17 | 39 | 17 | 5.64 | 17 | 220.00 | 17 | 190 |
| 18 | 43 | 18 | 5.12 | 18 | 220.00 | 18 | 190 |
| 19 | 43 | 19 | 5.12 | 19 | 220.00 | 19 | 190 |
| 20 | 43 | 20 | 5.12 | 20 | 220.00 | 20 | 190 |
| 21 | 46 | 21 | 4.78 | 21 | 220.00 | 21 | 190 |
| 22 | 47 | 22 | 4.68 | 22 | 220.00 | 22 | |
| 23 | 48 | 23 | 4.58 | 23 | 220.00 | 23 | |
| 24 | 50 | 24 | 4.40 | 24 | 220.00 | 24 | |
| 25 | 52 | 25 | 4.23 | 25 | 220.00 | | |
| 26 | 52 | 26 | 4.23 | 26 | 220.00 | | 245 |
| 27 | 52 | 27 | 4.23 | | | | 245 |
| | | | | | | 998 | 245 |
| | | | | | | 999 | 245 |
| | | | | | 220.00 | 1000 | 245 |
| 1001 | 109 | 1001 | 2.02 | 1001 | 220.00 | 1001 | 245 |
| 1002 | 109 | 1002 | 2.02 | 1002 | 220.00 | 1002 | 245 |
| 1003 | 109 | 1003 | 2.02 | 1003 | 220.00 | 1003 | 245 |
| 1004 | 105 | 1004 | 2.08 | 1004 | 217.92 | 1004 | 245 |
| 1005 | 106 | 1005 | 2.08 | 1005 | 220.00 | 1005 | 245 |
| 1006 | 104 | 1006 | 2.10 | 1006 | 217.90 | 1006 | 246 |
| 1007 | 106 | 1007 | 2.12 | 1007 | 224.23 | 1007 | 245 |
| 1008 | 100 | 1008 | 2.16 | 1008 | 215.69 | 1008 | 245 |
| 1009 | 101 | 1009 | 2.18 | 1009 | 220.00 | 1009 | 245 |
| 1010 | 102 | 1010 | 2.20 | 1010 | 224.40 | 1010 | 245 |
| 1011 | 100 | 1011 | 2.20 | 1011 | 220.00 | 1011 | 245 |
| 1012 | 96 | 1012 | 2.29 | 1012 | 220.00 | 1012 | 245 |
| 1013 | 94 | 1013 | 2.32 | 1013 | 217.68 | 1013 | 245 |
| 1014 | 95 | 1014 | 2.34 | 1014 | 222.34 | 1014 | 245 |
| 1015 | 94 | 1015 | 2.34 | 1015 | 220.00 | 1015 | 245 |
| 1016 | 92 | 1016 | 2.37 | 1016 | 217.63 | 1016 | 245 |
| 1017 | 92 | 1017 | 2.39 | 1017 | 220.00 | 1017 | 245 |
| 1018 | 91 | 1018 | 2.39 | 1018 | 217.61 | 1018 | 245 |
| 1019 | 93 | 1019 | 2.42 | 1019 | 224.84 | 1019 | 245 |
| 1020 | 90 | 1020 | 2.44 | 1020 | 220.00 | 1020 | 245 |
| 1021 | 90 | 1021 | 2.44 | 1021 | 220.00 | 1021 | 245 |
| 1022 | 88 | 1022 | 2.44 | 1022 | 215.11 | 1022 | 245 |
| 1023 | 86 | 1023 | 2.47 | 1023 | 212.58 | 1023 | 245 |

91 — 92 — 93 — 94

95 etc

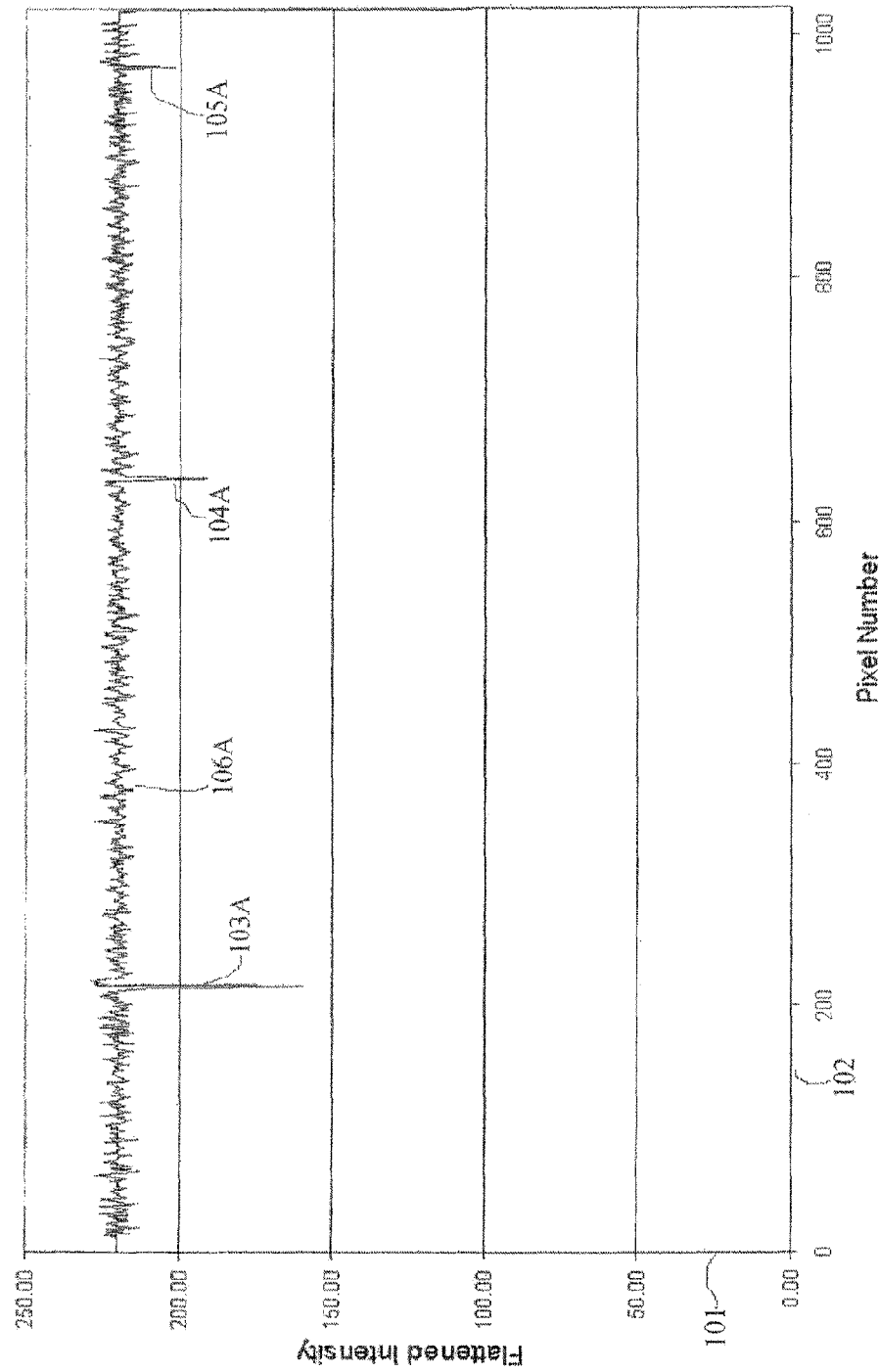

ENHANCED IMAGING METHOD AND APPARATUS

FIELD OF THE INVENTION

This invention relates generally to a method and apparatus for the identification of the surface characteristics of an object, and more particularly to a non-contact system to generate image data representative of surface reflectivity of an object that may be used as an input to suitable industrial process control apparatus.

BACKGROUND OF THE INVENTION

The invention will be described primarily in connection with using light to obtain image data representing surface reflectivity of the external surfaces of boards of sawn timber in order to enable the computing of accurate image data of the three-dimensional surface profile of each individual board, for the purpose of adjusting sawing equipment in saw mills. This is important in a world of diminishing resources to optimize the quantity or value of the lumber produced. Image data is assembled from a sequence of surface scans of a board as it moves past a linear sensor of scanning apparatus. A typical scan would record image data 2048 pixels long by 1 pixel wide. However, area cameras could be used and larger swaths of pixel data would accordingly be input for image processing. Having computed the image of a board from scan data, algorithms can be applied that decide on the optimal placement of cuts by automated equipment in order to achieve desired characteristics of boards with minimal waste pieces. The surface features of the board captured in the image data disclose irregularities such as knots to be avoided or placed in order to meet the criteria for pieces to be made from the board. However, the invention is also applicable to measurement of other objects where rapid and accurate image capture may be beneficial.

The state of the art in target object imaging for industrial processing has been the obtaining of geometric, dimensional information from which a computer model of the object is constructed as if the object were homogeneous in composition.

The simplest non-contact automatic method commonly used to determine the shapes of boards is known in the prior art as shadow scanning. The board moves past a row of beams of light and the cross-sectional width of the board is determined by measuring the shadow cast by the board on an array of sensors on the other side of the board, which sensors are lined up with the projected light beams. Beams of light must be applied from several directions and sensed by a corresponding set of sensor arrays to obtain even a rough profile. The shadow method cannot measure or even detect concave features such as hole in the board. It measures the outer envelope of the profile of the board.

Other methods known in the prior art for determining the shape of an object without contact depend on the principle of triangulation, which has been known historically prior to the present century. The application of this principle can be illustrated by considering a single beam of light transmitted in a known direction in space from a known location at an object being measured. Some suitably selected form of receiving system positioned so as to view the object from a direction different from the direction at which the light was transmitted detects the direction from the receiving system at which the reflection from the projected light spot appears on the object being measured. The distance between the transmitter and the receiver is known and fixed. Hence two angles (determined from the transmitting and receiving directions) and one side of a triangle (the distance between the transmitter and the receiver) are determined, and thus the location of the spot on the object relative to the measuring apparatus is easily calculated. Triangulation is generally used to obtain geometric views and cannot by itself provide images of surface appearance variations that are not correlated with changes in geometric shape of the target object.

The present invention now provides a method and means for capturing enhanced surface appearance data and adding it to the geometric image of a target object.

Many industrial scanning applications require fast image capture (digital pictures) of target surfaces. All physical targets reflect incident light that falls on a surface in one of two kinds of reflection: specular reflection or diffuse reflection. Geometric imaging, the measuring and calculating from a distance of the profile of target objects having irregularities of shape moving rapidly along a production line, is plagued by instances of specular reflection of the light from the illumination source by various areas on the object to be imaged. Areas of specular reflection from the target object appear as overly bright areas on camera images and also obliterate image accuracy regarding surface appearance characteristics quite apart from variation in surface shape.

Specular reflection-is the mirror-like reflection of light (or sometimes other kinds of wave) from a surface, in which light from a single incoming direction (a ray) is reflected into a single outgoing direction. Specular reflection results from the tendency for incident light to be reflected at the same angle as the incidence angle on the opposite side of a normal to the surface. A mirror is an example of a very good specular reflector. Diffuse reflection is the tendency for incident light to be reflected in an omni-directional manner above the target surface. An example of specular vs. diffuse reflection can be found in comparison of "glossy" vs. "flat" paints—glossy painted surface is much more specularly reflective when compared with a surface painted with flat paint.

High speed image capture systems, used to scan dynamic scenes, benefit from a high intensity illumination source because camera exposure and integration time can then be reduced, enabling less smearing of the captured image and faster scan rates. This is particularly significant in industrial machine vision applications, when 2-dimensional images are obtained by combining a plurality of sequentially acquired linear scans. Machine vision is not restricted to 2 dimensional images generated from a plurality of sequentially acquired linear scans.

High quality image capture is desired or required in various machine vision applications to allow image processing to identify, isolate and classify features of interest in the image. Some aspects of image quality are predictable intensity response, ability to merge images captured from adjacent but similar image capture systems, with minimum "stitching" features which may negatively affect image processing. A good quality image having such characteristics can be obtained in an image acquisition system when only diffuse reflection—as opposed to specular reflection—from the target object is included in the image.

A classic challenge with image capture systems is the illumination system. Generally it is undesirable to have point-source lighting and desirable to have "flat" or "soft" lighting, that is, diffuse lighting. Non-diffuse lighting can result in peculiarities of contrast and shadow on images of the target object due to the light source's position. A source of light can be considered effectively a point source if the resolution of the imaging instrument is too low to resolve its size, or if the object is at a very great distance. To avoid hot spots created by specular reflection of one or of a few point source illuminators, many image capture illumination systems employ a large plurality of light sources and/or diffusing elements to try to minimize hot spots created by the specular reflectivity.

With a high speed moving target, the illuminator should be a flash rather than sustained ambient light, in order to capture the required image data for the system.

Historically, visual features of a board are only considered after cutting, at a sorting stage. The present invention enables the moving of such decisions upstream in the lumber milling process, and enables more usable and higher value end product than the prior technology.

SUMMARY OF THE INVENTION

The present invention provides for accurate, high quality images of the objects scanned by processing raw image linear scans ("Raw Scans"), which can be assembled sequentially to form raw images ("Raw Images"). The Raw Scans are acquired from separate cameras simultaneously. The cameras may be CCD, CMOS linear sensors, or use other photosensitive devices that responds to varying levels of light emanating from its field of view. Processing the Raw Scans as summarized below to address distortions, and combining the resulting processed images is done in order to arrive at the desired high quality Enhanced Image, void of specular reflections, with uniformity of image where the object scanned has uniformity of surface, and accurate portrayal of aberrant areas where the object scanned has such aberrations.

Two (or more) corresponding Raw Images (or two or more Raw Scans before their assembly into Raw Images) from separate cameras are processed with "Flattening" and "Gridizing". The resulting two (or more) corresponding Flattened and Gridized Images are then compared and portions of each are selectively combined to render an enhanced, accurate image (the "Enhanced Image") of the target object. The "Selective Combining" uses the segments of the processed Raw Scans that have only diffuse reflection, and discards the segments of the scans that have specular reflection. Areas of specular reflection are thus essentially eliminated in the Enhanced Images.

The accurate imaging method and apparatus presently disclosed will overcome distortions not only due to specular reflection (in the Selective Combining) but also due to variations deriving from the radiation pattern of the illumination source and responsiveness of the cameras along the pixel axis (by Flattening) and due to parallax (by Gridizing). The elimination of the latter variations via Flattening and Gridizing is necessary in order to use the Selective Combining method disclosed in more detail below. Flattening and Gridizing are therefore performed before the Selective Combining of the image data.

In Flattening, the Raw Scan data is compensated for illumination radiation and geometric pattern variance, and particular sensitivities of each camera in use. Unrealistic image results, apart from the effects of specular reflection, are mainly due to radiation geometric pattern variance from the illumination source to the scanned object, and to irregularities in camera sensitivity. In the present invention, both illumination source and camera are fixed in position, so it is possible to compensate for these image-distorting factors by calibrating out the effects of these variations and get a flat video response. Before applying the enhanced imaging method summarized above, a flattening calibration is done to obtain pixel amplitude correction coefficients which are a function of X (axis from target surface to scan head) and Y (axis across target object) coordinate locations in the scan zone. A succession of images of a stock, uniform "gray card", available from photographic supply companies, are taken with each camera and corresponding illuminator that is used in the system. A "gray card" is manufactured with specified optical qualities, such as 18% reflectivity on one side and 90% reflectivity on the other side. The higher reflective side (e.g. 90% reflectivity) is used in order to get a stronger video signal when doing the flattening calibration. A number of scans are taken across Y at each X coordinate, in order to average out system video noise. The flattening calibration is repeated at a range of X=X 1, then X=X 2 and so on, in order to get a base "flattened" video signal level for each X and Y coordinate.

It is adequate for purposes of enhanced image board scanning to take such calibration scans at each ¼ inch along the X axis. For even greater accuracy, finer increments of flattening calibration could be performed. Either way, computer calculations then provide interpolated values for finer coordinates along X.

The flattening calibration scans are taken with each camera and corresponding illuminator that is used in the system. The "gray cards" can be joined to form a strip long enough to cover the scan zone, and the joining gap or overlap lines can either be attributed with adjacent test values, or the strip can be moved after a first set of tests to place non-joint areas in the former joint areas, and obtain "flattened" video for those coordinates as well. In practice it is often sufficient if the test scans are taken ¼" apart. In Flattening the coefficients of variation for the test "flattened" video at all the coordinates across the scan zone will be applied to the same coordinates of Raw Scan data obtained from the actual target. After Flattening is applied to the Raw Scans, the results will be called "Flattened Scans." The Flattened Scans may be assembled sequentially into "Flattened Images".

Regarding the Gridizing step, the problem with combining segments of different Raw Images of the same object taken from different cameras is that the different Raw Images will have differing parallax. Parallax is the perspective effect of angle and distance of different areas of the target with respect to the camera, an apparent displacement or difference of orientation of an object viewed along two different lines of sight, and is measured by the angle or semi-angle of inclination between those two lines. When two cameras at different locations are performing Raw Scans to be combined later on a pixel by pixel basis to form a single accurate image of the target object, the parallax must be calculated and compensated. When a target object is at a known range, whether a board or a test sheet of paper on a plate of glass with a known distance to a camera, the effect of parallax can be calculated and compensated, in order to generate an orthographic image. "Gridizing" is performed to compensate for the variation in the distance from the target to the imaging system. Undoing image parallax results in an orthographic image (the "Ortho Image", or "Ortho" scan if dealing with a single scan), as if the image was acquired at an infinite distance.

Parallax can be undone using either a calculated or calibrated method and avoids using a special type of parallax-corrective lens known as a telecentric lens. A telecentric lens is a compound lens with an unusual geometric property in how it forms images. The defining property of a telecentric system is the location of the entrance pupil or exit pupil at infinity. This means that the chief rays (oblique rays which pass through the center of the aperture stop) are parallel to the optical axis in front of or behind the system, respectively. Such lenses are large, expensive, and typically have a small field of view, which renders them unsuitable for scanning long boards for example.

In order to calculate or calibrate to remove parallax from an image, prior knowledge of the physical distance of the target to the imaging system is required. When a target is at a fixed distance from a camera in a system, such as on a flat bed scanner, parallax compensation can be calculated/calibrated once for the camera and applied to every image taken with it thereafter. When a target may be present at different distances from the imaging system, or portions of the target are at varying distances from the imaging system, each such distance at the time of each Raw Image must be known to perform Gridizing.

Generation of the Enhanced Images thus comprises parallel stages for each of at least a first and a second camera's respective captured images. The illuminator that was previously calibrated with the cameras for purposes of Flattening shines on the target to obtain a scan for each of Camera 0 and Camera 1. The method then proceeds with:

Camera 0 Raw Scan - - - Camera 0 Raw Scan Flattening - - -
  Camera 0 Flattened Scan Gridizing paralleled by
Camera 1 Raw Scan - - - Camera 1 Raw Scan Flattening - - -
  Camera 1 Flattened Scan Gridizing and then the respective (two, or more if more cameras are used) resulting Ortho Scans from each Raw Scan—Flattening—Gridizing parallel stage above are combined in a separate fourth step of Selective Combining:

Camera 0 Gridized (Ortho) Scan - - - combined with—Camera 1 Gridized (Ortho) scan to result in an Enhanced Scan. The Selective Combining of best pixel amplitude from corresponding pixels in the respective Ortho Scans produced Enhanced Scans. The Enhanced Scans can be assembled in order to render Enhanced Images.

It will be appreciated that the Method summarized above can be applied to Raw Images that have been assembled from individual Raw Scans, the Raw Images from the respective cameras being then Flattened into Flattened Images, the Flattened Images being then Gridized into Gridized Images (Ortho Images), and the respective Ortho Images then being selectively combined into Enhanced Images. The place in the method at which scans are assembled into larger images is optional. It is simpler to apply the whole process to individual scans before their assembly into images, but it is not necessary to the invention, and with the appropriate calculations the assembly of scans into images could be done at any stage or step of the method herein disclosed, and the remaining stages or steps then applied to the resulting images rather than to the scans.

The system of the present invention gives better results and works faster than using one physical camera while processing images taken with multiple non-simultaneous illuminators shining at different angles on the subject material. It is faster because the presently disclosed system does not have to wait to acquire multiple images from each illuminator. A single image capture cycle is required and a higher production rate can be achieved.

The present invention works for moving targets—as both camera images are captured simultaneously, both acquired images are seeing the same portion and hence features of the target object. If multiple non-simultaneous illuminations are used in a moving target system, for example, when the target is on an assembly line or conveyor belt, the target will have moved between illuminations, resulting in the loss of correspondence between features imaged on each of the non-simultaneous acquired images.

A distinction must be made between a) designed "scanning" movement of the target or of the scanner, along a (typically horizontal) plane (such as a conveyor belt), with an intended constant distance between a scanner camera sensor mount head and a surface of interest on the target, and b) unintended "target range" movement in the distance between scanner head and target, such as may occur due to vibration of equipment or to varied 3-dimensional topographical features of the target. The "moving targets" above refers to the designed "scanning" movement.

In the accurate imaging system of the present invention, scanning movement is tightly controlled, with microseconds tracked. The level of temporal latency is designed to enable accuracy on the order of $1/1000$th inch for spatial control of the target position during a scan. It is important that both corresponding Raw Images from the parallel stages noted above be combined properly to capture the same portion of the target for the eventual Enhanced Image. It is theoretically possible to use area cameras to acquire multiple images from multiple illumination sources of a moving target object, for later input into calculations about the object, but it would be far more computationally intensive than the method herein disclosed. When too many pixels form the image data, any inadvertent target movement (as opposed to intended, controlled target movement for successive scans) vastly increases the problem of compensatory calculations. This is of even greater concern in the case of more than two cameras being used simultaneously in this accurate imaging process.

To acquire the Raw Images, and maintain a known image aspect ratio—a Position Encoder is used to track the position of the target as it moves. Position encoders are used to generate an electronic signal that indicates an absolute mechanical position, or an incremental mechanical movement relative to a reference position. Preferably the encoder is used to trigger scan captures at correct physical intervals or less desirably to select the desired image from an oversampled set of scans, said selection criteria to determine the acquired image aspect ratio.

For elimination of specular reflection, the physical arrangement of projector and two cameras should be such that the cameras have sufficient physical separation to avoid both cameras receiving the same reflected light and imaging a highly specular reflective portion of the target. In the photographic terms of "far field" and "near field", the placement of the cameras in relation to the scan zone is such that the target is essentially in the cameras' "far field". It is a physical fact that regardless of the surface characteristics of the target, cameras separated from each other and from an illuminator along an axis parallel to a raw scan line on the target object cannot both receive an overly bright, specularly reflected patch of light from the same patch of the target object illuminated by a point-source (or effectively point-source) illuminator. For each camera there is one and only one specularly reflective beam path (at which the angle of reflection equals the angle of incidence) between the illuminator and the camera, and each of those beam paths strikes the target object at different areas.

Following Flattening and Gridization of the corresponding Raw Scans from the multiple cameras, the resulting Ortho Images are comparable on a geometric response level, as they have acquired images from the same target, and both (all, in the case of more than two cameras) of the corresponding Ortho Images represent a view from a distance of infinity. In other words, a given feature from the target appears in both images at the same location. The images are therefore now comparable on a pixel by pixel basis. Higher video signal amplitude pixels as between Camera 0 Ortho (scans or images) and Camera 1 Ortho are the result of specular reflection as opposed to diffuse reflection. This is key to enable selection of portions of each Ortho Image for inclusion in one Enhanced Image, in order to generate an accurate image of the target without areas of specular reflection distorting the image. After the Flattening and Gridizing are performed on the Raw Scans, the resulting Ortho Images of the target from each camera will have a pixel to pixel comparison possible with respect to amplitude response for each defined geometric location on the target object. The Selective Combining can then be performed. Corresponding pixel amplitudes representing respective segments of the target object in each of the two or more corresponding Ortho Images are compared, and the lower value is selected for inclusion in the Enhanced Image. In the Gridizing step, it is also possible to achieve improved imaging by selecting an average of the corresponding pixel amplitudes or by taking part of one pixel and part of another, particularly if both are within a known normal range for the target being imaged. Excellent results can also be obtained by applying the three steps of the parallel stage and then the Selective Combining on every other pixel in a pair of 2048-pixel-long X 1 pixel wide Raw Scans, combining the other pixels of data—this effectively uses 1024 pixels of data per scan and cuts in half the data computed, yet provides more accurate enhanced images than using 1024-pixel or even 2048-pixel data without the method of the present invention.

The enhanced imaging method and apparatus of the present invention generates multiple images of a target object and makes them comparable on a pixel-by-pixel basis. The comparing requires either a known distance to a flat surface, a known set of distances to a complexly engineered surface (such as a curved windshield, which could be inspected by the method and apparatus for surface features such as cracks). or a geometric scan of a varying surface to obtain its geometric profile.

The state of the art in geometric scanning uses coded light from a laser to obtain a geometric scan of the target object at each X and Y coordinate within the scan zone. It is also possible to use a "sheet of light" method from the prior technology to obtain a geometric profile of the target object, but that method would involve having an area camera upstream or downstream of the imaging scan head. All these and related methods and apparatus to obtain the geometric profile of a target object are herein referred to as "structured light geometric scanning" The image capture method and apparatus presented here allows high intensity point source or near point source lighting, yet eliminates or greatly reduces the occurrence of specular reflectivity in the final enhanced image for the image capturing system. A single LED or a laser is an example of what is meant by "point source" in this disclosure. An array of LEDs is an example of a near point source for purposes of this invention. Indeed, in the present invention, a point source or near point source is desirable because:

a) it can be integrated efficiently into a scan head housing; and
b) it allows the cameras and the illuminator to be placed all in a co-planar arrangement in the scan head, which renders the calculations of the invention method to be simpler than if those elements were not aligned.

One preferred arrangement for the illumination elements in the apparatus of the present invention is to use a coded light laser for obtaining a geometric profile of the target object, and an LED array comprising 15 LEDs in a row, aligned with but between the first and second cameras, for obtaining the raw data that will be processed into the enhanced image data by the method summarized above. The geometric profile data is used to identify coordinates on the target object surface that will be mapped to the Raw image data acquired by each of the separated cameras and thus to the corresponding Flattened and Gridized image data in the parallel paths from Raw to Gridized (Ortho) Images, and thence to the Enhanced Image. It is possible to use the invention without using a coded laser or other geometric profile detection means if the geometric profile of the target object is already known and computed. For example, the invention could be used to detect surface anomalies such as cracks in a precision-manufactured article such as a glass windshield. There is also an important distinction between using "structured r light (such as a coded laser) to scan and compute the shape and position (geometric profile) of a surface and using an uncoded laser as one kind of target illuminator for the first and second cameras while obtaining the first and second raw data. An uncoded laser can be used to obtain monochrome raw image data by each of the first and second cameras, whereas LEDs provide suitable illumination for obtaining color raw image data. In order to obtain and use both monochrome and color raw data, the respective illuminators must be cycled, for example, flashed alternately.

The invention can work with area lighting, or with continuous illumination from a point source or near point source, but the need for rapid multiple scans in an industrial process demands high intensity illumination to enable fast scan and exposure times by the cameras. LEDs for example can operate at a much higher intensity if they are flashed on and off as needed by the cameras, with the off times allowing for heat dissipation. Heat is a limiting factor in both the life and performance of LEDs. Turning off an illuminator between the scans that need the particular illuminator also conserves electrical power. In any event, the alternating illumination is necessary to allow multiplexing between the geometric profiling of the target object with structured light, and surface appearance raw data acquisition by the first and second cameras. It is also useful to the acquisition and integration of both monochrome and color raw data by the method and apparatus of the invention. A computer control is used to trigger the illuminators at the desired times.

The invention provides a method for generating accurate, high quality images comprising the steps of:

a) acquiring a first raw scan of a portion of a target object across a scan line in a scan zone with a first camera and simultaneously acquiring a second raw scan of the same portion of the target object across the scan line in the scan zone with a second camera, the second camera being separated from the first camera in a camera zone such that the first and second camera have substantially different perspectives of the same portion of the target object;

b) converting the first raw scan from analog to digital format resulting in first raw image data and converting the second raw scan from analog to digital format resulting in second raw image data;

c) processing the first raw image data with a first set of flattening coefficients derived from measurements of variations in illumination and in first camera response across the scan line to a uniform diffusely reflecting target in the scan zone, resulting in first flattened image data from the target object, and processing the second raw image data with a second set of flattening coefficients derived from measurements of variations in illumination and in second camera response across the scan line to the uniform diffusely reflecting target in the scan zone, resulting in second flattened image data from the target object;

d) compensating for parallax in first flattened image data with a first set of calculations, resulting in first orthographic image data,; and compensating for parallax in second flattened image data with a second set of calculations, resulting in second orthographic image data;

e) comparing first orthographic image data corresponding to a coordinate location on the target object with second orthographic image data corresponding to the coordinate location on the target object;

f) selecting a pixel intensity value, for use as enhanced image data representing the coordinate location on the target object, from:
  i) the first orthographic image data corresponding to the coordinate location;
  ii) the second orthographic image data corresponding to the coordinate location;
  iii) a result of a formula using a combination of the first and second orthographic data corresponding to the coordinate location.

Regarding step d) above, the parallax inherent in the first flattened image data is different from the parallax inherent in the second flattened image data, and both must be compensated with the respective sets of calculations in order to arrive at first and second orthographic image data. It is those different orthographic sets of data which can then both be compared on a pixel by pixel basis and identified with a single geometric point on the actual target surface.

Regarding step f) above, one example would be to choose a pixel intensity value from the first orthographic image data over the corresponding data from the second orthographic data (both corresponding to the coordinate location of that pixel in the geometric data), because the pixel intensity value for that location was lower in the first orthographic data than in the second orthographic data. Another example, falling under f) iii) above, would be to take a weighted average intensity value for that pixel, drawn from both the first and second orthographic data. The use of such a formula could depend on the particular target object surface characteristics and the desired type of Enhanced Image to be obtained from it. In practice, the steps of Claim 1 are repeated with scanning of sequential scan lines across the target object, resulting in sequences of enhanced image data representing corresponding coordinate locations on the target object, and assembling an enhanced image of the target object from the sequences of enhanced image data. The movement of the target object during scanning is controlled to maintain a known image aspect ratio during scanning and to avoid distortion of the enhanced image. An electronic signal from a position encoder is used during the scanning to indicate target object position relative to a reference position for the scan zone. For example, the target can ride a conveyor belt along a z-axis below the scan head. Alternatively, there may be an industrial situation in which it is preferable to move the scan head along the z-axis over the target object, for example, where the target is very heavy. The position encoder need not be aligned with the z-axis. It could sense and calculate z-axis motion although its sensor to target path was for example at 45 degrees to the z-axis. In any event, scans are triggered by the position encoder at known incremental intervals of a target object movement through the scan zone.

To counter specular reflection, the pixel intensity value selected for use as enhanced image data would be the lower of two corresponding orthographic pixel data values from first orthographic data and from second orthographic data, thereby selecting lower specular reflection from the target object.

The geometric positions of relevant portions of the target object can be obtained by structured light geometric scanning, enabling mapping of first raw data pixels to corresponding second raw data pixels. If a coded laser is used for the structured light (rather than using bands of colored light, for example), it should be noted that this use of a laser is different from the use of uncoded laser light in a variant of the system in which an uncoded laser illuminator is used in conjunction with a monochrome camera to obtain at least one set of raw image data in monochrome. In many situations, however, the most informative raw image data would be obtained by using an LED to illuminate the target object for the first and second cameras during an image capture scan.

Alternate firing, from a structured light geometric scanner illuminator to obtain target object surface profile and from a raw image data illuminator to obtain raw data for image, is made effectively simultaneous with respect to z-axis scanning movement of the target object by having a time between flashes from the respective illuminators sufficiently short that a computed adjustment of coordinate positions to compensate for scanning movement of the target object between firings is within computational limits for correlating resulting structured light geometric profile data and corresponding raw image data to pixel resolution.

It is convenient to apply the Enhanced Imaging method and apparatus to individual successive scan lines of raw data, ending up with a "scan" line of Enhanced data, with sequential Enhanced lines being then available for assembly into a large two dimensional image. However, the assembly of successive "scan lines" could be done at any stage after obtaining the raw data, with the remaining steps then applied to the two dimensional image data.

In an industrial application with wide target objects, both:
  a) the processing of the first raw image data with a first set of flattening coefficients derived from measurements of variations in illumination and in first camera response across the scan line to a uniform diffusely reflecting target in the scan zone, resulting in first flattened image data from the target object, and
  b) the processing of the second raw image data with a second set of flattening coefficients derived from measurements of variations in illumination and in second camera response across the scan line to the uniform diffusely reflecting target in the scan zone, resulting in second flattened image data from the target object, would be performed to a standard level of image flattening with multiple identical adjacent scan heads each using an illuminator, a first camera and a second camera, and the processing method of the invention. Multiple flattened images of adjacent areas on the target below adjacent scan heads obtained by such processing can then be joined to form an overall image of the target without significant discontinuity of image accuracy between multiple enhanced images from respective adjacent scan heads. The invention enables a geometrically exact stitch line between such joined images and obviates grotesque overlapping of portions of adjacent Enhanced Images. The pixels on the stitch line itself can be selectively combined from adjacent sets of Enhanced Image data. In a preferred embodiment, multiple images of adjacent areas on the target object would be joined together by truncating and aligning along a stitch line that is exact to each pixel (rather than overlapping adjacent images), in order to minimize discontinuity of target object features, and to minimize discontinuity of image intensity values for adjacent geometric locations on the target object to below image background noise values.

The method disclosed above can be preformed with the apparatus indicated herein. Each step of processing of the relevant data can be performed by a central computer or by a dedicated processing module. The apparatus should include:

a) at least two cameras, including a first camera set up for acquiring a first raw scan of a portion of a target object across a scan line in a scan zone with a first camera and simultaneously acquiring a second raw scan of the same portion of the target object across the scan line in the scan zone with a second camera, the second camera being separated from the first camera in a camera zone such that the first and second camera have substantially different perspectives of the same portion of the target object;

b) an analog to digital converter set up for converting the first raw scan from analog to digital format resulting in first raw image data and converting the second raw scan from analog to digital format resulting in second raw image data;

c) a flattening image processing module that processes the first raw image data with a first set of flattening coefficients derived from measurements of variations in illumination and in first camera response across the scan line to a uniform diffusely reflecting target in the scan zone, resulting in first flattened image data from the target object, and that processes the second raw image data with a second set of flattening coefficients derived from measurements of variations in illumination and in second camera response across the scan line to the uniform diffusely reflecting target in the scan zone, resulting in second flattened image data from the target object;

d) a gridizing image processing module that compensates for parallax in first flattened image data with a first set of calculations, resulting in first orthographic image data, and compensates for parallax in second flattened image data with a second set of calculations, resulting in second orthographic image data;

e) a selective combining image processing module that compares first orthographic image data corresponding to a coordinate location on the target object with second orthographic image data corresponding to the coordinate location on the target object and selects a pixel intensity value, for use as enhanced image data representing the coordinate location on the target object, from:

i) the first orthographic image data corresponding to the coordinate location;
   ii) the second orthographic image data corresponding to the coordinate location;
   iii) a result of a formula using a combination of the first and second orthographic data corresponding to the coordinate location.

As an example under e) iii) immediately above, the selective combining image processing module could appropriately be programmed to take an average value of intensity for any give pixel location from the first and second orthographic data, if that pixel fell on an edge of the Enhanced Image to be used in abutment with an Enhance Image from an adjacent apparatus of an extended target object, such as a log, or long board.

Preferably, the apparatus further comprises a computer set up to obtain sequential scan lines across the target object and sequences of enhanced image data representing corresponding coordinate locations on the target object, and to assemble an enhanced image of the target object from the sequences of enhanced image data, and a position encoder set up to track movement of the target object during scanning in order to maintain a known image aspect ratio during scanning and to avoid distortion of the enhanced image. The computer can also be set up to perform image stitching from adjacent scan heads, each of which has an instance of first and second cameras, and imaging illuminator. Preferably, each scan head would also have a coded light, laser illuminator for providing geometric profile data from the target object to the computer.

The selective combining image processing and other modules can be embodied in hardware or a combination of software and computer hardware, programmed to select for use as enhanced image data a lower of two corresponding orthographic pixel data values from first orthographic data and from second orthographic data, thereby selecting lower specular reflection from the target object.

A structured light geometric scanner, which is known technology, can be used to obtain for obtaining geometric positions of relevant portions of the target object. It is new however to use this information for the mapping of first raw data pixels to corresponding second raw data pixels preparatory to the Flattening, Gridizing process modules. Likewise, it is commonplace to use LED illuminator in conjunction with a color camera to obtain color images, but it is new to use them with a second camera in the manner described by which different by corresponding sets of raw image data are sent first through a Flattening module and then through a Gridizing module, and finally through a Selective Combining module, to arrive at an Enhanced Image.

BRIEF DESCRIPTION OF THE DRAWINGS

FIG. 3 is an optical schematic diagram showing some of the light paths in a two-camera, two illuminator example of the apparatus.

FIG. 5B is a graph of three Projector Radiation patterns, at three distances along the X-axis from FIG. 2.

FIG. 7B is a graph showing the calculated Flattening Coefficients for Camera 1.

FIG. 9 shows the beginning and end of a long Spreadsheet of GrayCard image data.

FIG. 10A is a graph of Flattened Image data from Camera 0.

DETAILED DESCRIPTION OF THE INVENTION

Figure 1:
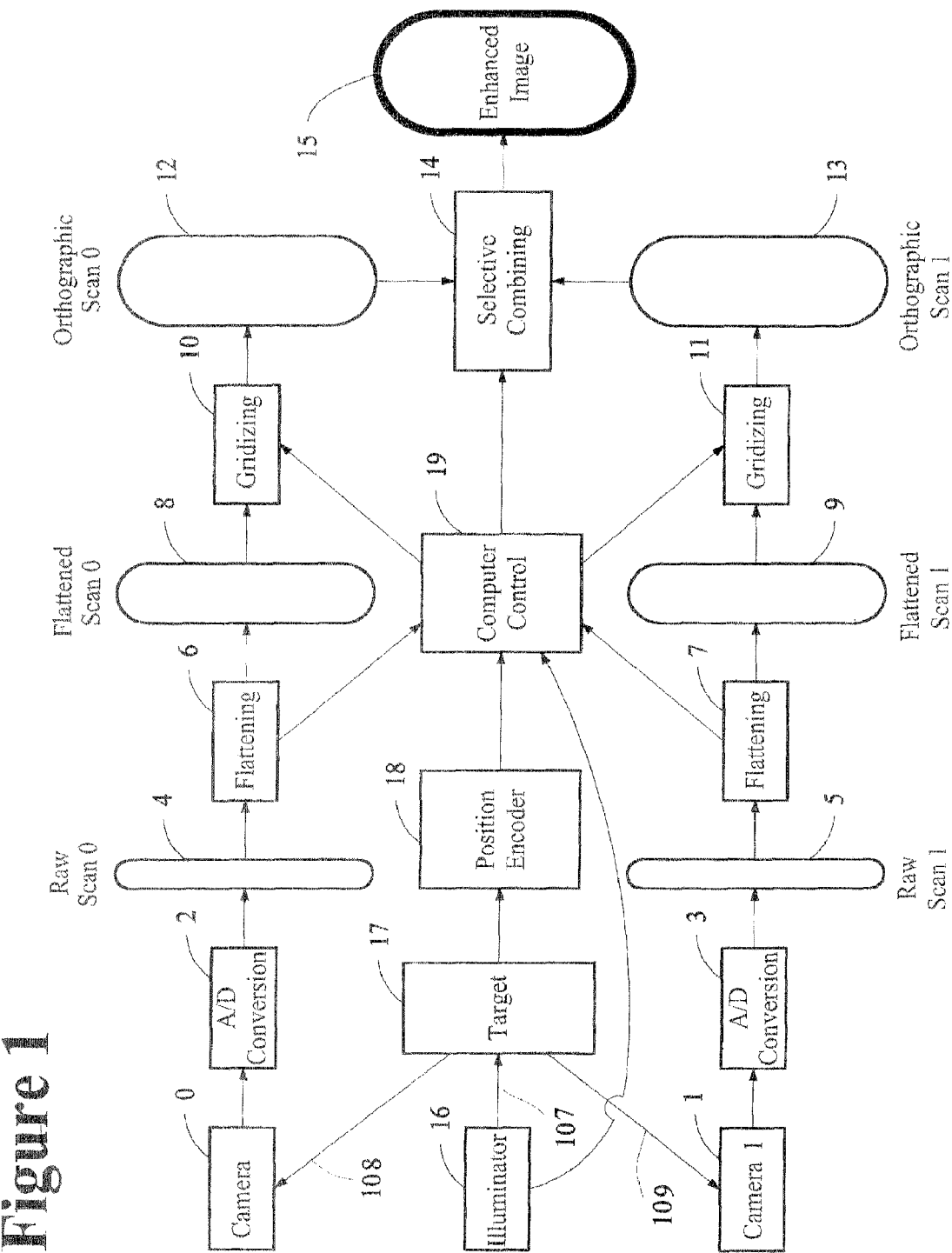
FIG. 1 is a block diagram illustrating the basic steps and elements in the enhanced imaging method and apparatus of the present invention.

Referring to FIG. 1, an illuminator 16 shines light 107 on a target object 17. A mixture of diffuse and specular reflection occurs along various beam paths such as at 108 and 109 to Camera 0 and to Camera 1 respectively. Light input to Camera 0 is put through A/D Conversion 2 in an analog/digital converter, which outputs a set of Raw Scan 0 data 4. The Raw Scan 0 data 4 then proceeds through the Flattening 6 process, which corrects each pixel for variance in illumination pattern and camera sensitivity. The Flattened Scan 0 data 8 then proceeds to a Gridizing 10 process, which corrects the data for parallax effect, that is, for the widening of pixel spaces at more oblique angles across the target surface from Camera O's perspective. The resulting Orthographic Scan 0 data 12 then proceeds to the Selective Combining module 14.

Likewise, light input to Camera 1 is put through A/D Conversion 3 in an analog/digital converter, which outputs a set of Raw Scan 1 data 5. The Raw Scan 1 data 5 then proceeds through a Flattening 7 process corresponding to Flattening 6 for the other Camera(0)'s output path. The Flattened Scan 1 data 9 then proceeds to a Gridizing 11 process corresponding the Gridizing 10 above for the other Camera (0)'s data path. The resulting Orthographic Scan 1 data 13 then also proceeds to the Selective Combining module 14.

The Selective Combining module 14 uses a pre-selected method of comparing Ortho Scan 0 data with Ortho Scan 1 data, on a pixel by pixel, or group of pixel by corresponding group of pixel basis, and the data that best matches Selective Combining criteria, such as lower image data value for each corresponding pixel from Ortho Scan 0 and Ortho Scan 1, is used, on the assumption that higher data value indicates specular rather than diffuse reflection.

A Computer Control 19 uses a Position Encoder 18, a known device in industrial assembly lines, to track the position of the target object 17 in the scan zone and to map readings from Camera 0 and Camera 1 to particular locations on the target object as the scanning proceeds. The Computer Control also times and fires the Illuminator 16, applies the Flattening coefficients to Raw Scans 0 and 1 in the Flattening 6 and 7 processes, calculates and applies corrections for parallax in Gridizing 10 and 11, and enables user control over the Selective Combining 14 criteria to be applied to result in the Enhanced Image 15.

Figure 2:
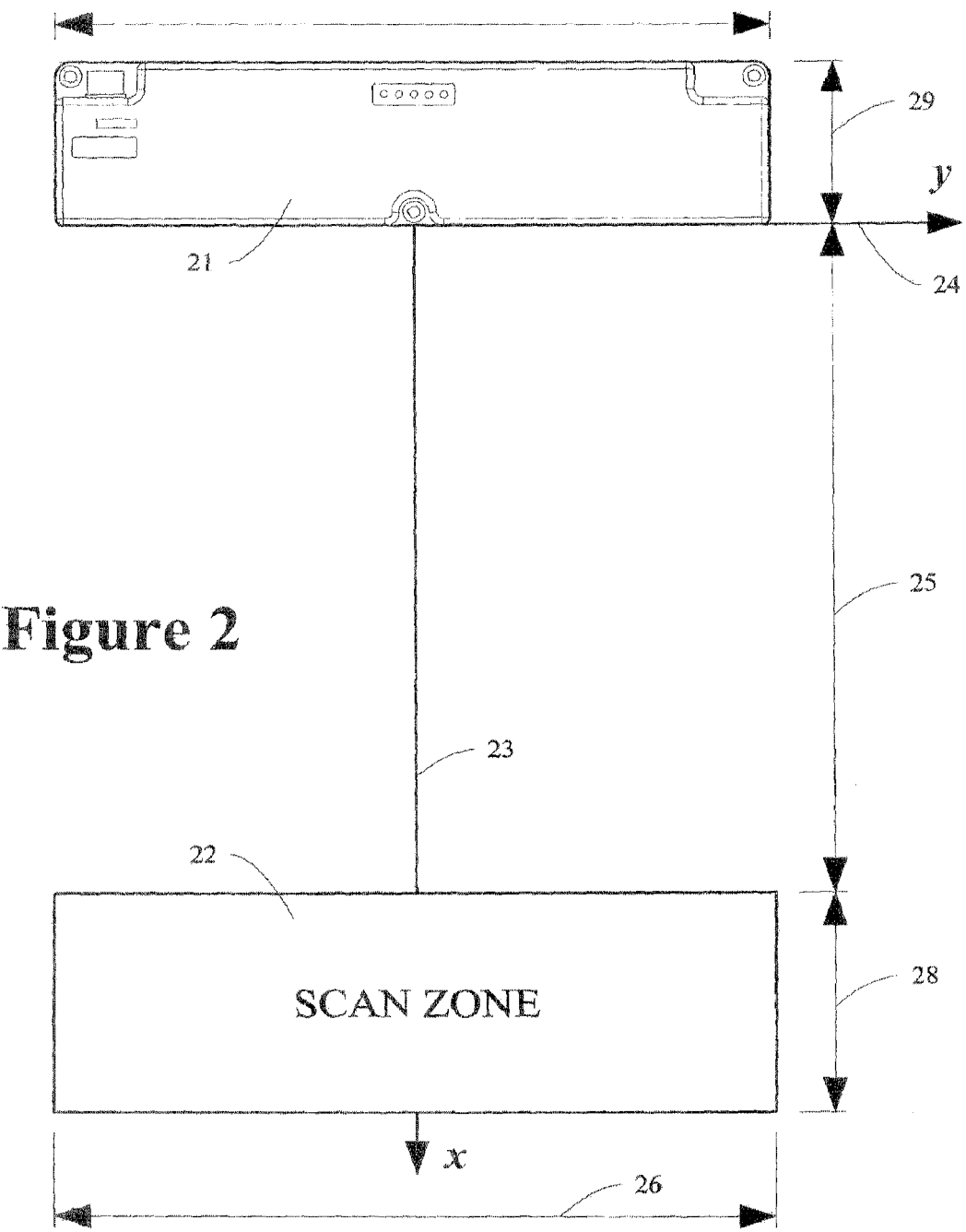
FIG. 2 is a schematic diagram showing an example of the apparatus' scan head coordinate system geometry and scan zone.

Referring to FIG. 2, a scan head 21 houses the cameras and illuminators that are used to acquire the sets of Raw Image Data. The scan head 21 is positioned directly over a scan zone 22 through which the target object can be conveyed. (Alternately, of course, the scan head 21 could be tracked over the scan zone 22 in which a stationary target object is scanned.) The vertical X-axis 23 runs from the center of the scan head 21 through the center of the scan zone. The scan zone 22 has a depth of field 28 (e.g. 8 inches) within which the target object will be in suitable focus for the cameras of the scan head. The horizontal Y-axis 26 traverses the width of the scan zone 22. A typical width for the scan zone would be 2 feet and a typical distance 25 between scan head 21 and scan zone would be 2 to 3 feet, but other distance arrangements with suitable cameras and illuminators would of course work. Likewise, a useful scan head height 29 is approximately 6 inches for lumber mill applications, sized such that cameras, lens, illuminators, scan windows, and related circuit boards are all contained within a sturdy housing.

Referring to FIG. 3, Camera 0 (item 33) has a field of view 35 that covers the entire scan zone 22, from line 35a to the target object scan zone upper left point 39, to line 35b to the target object scan zone upper right point 40. Likewise, Camera 1 (item 34) has a field of view 36 that covers the entire scan zone 22, from line 36b to the target object scan zone upper right point 40, to line 36a to the target object scan zone upper left point 39. A laser illuminator 31 provides coded light over the entire scan zone 22, with a coded laser field of projection 37, from line 37a to the target object scan zone upper left point 39, to line 37b to the target object scan zone upper right point 40. An LED illuminator 32 provides broad spectrum light over the entire scan zone 22, with an LED field of projection 38, from line 38b to the target object scan zone upper right point 40, to line 38a to the target object scan zone upper right point 39.

Figure 4A:
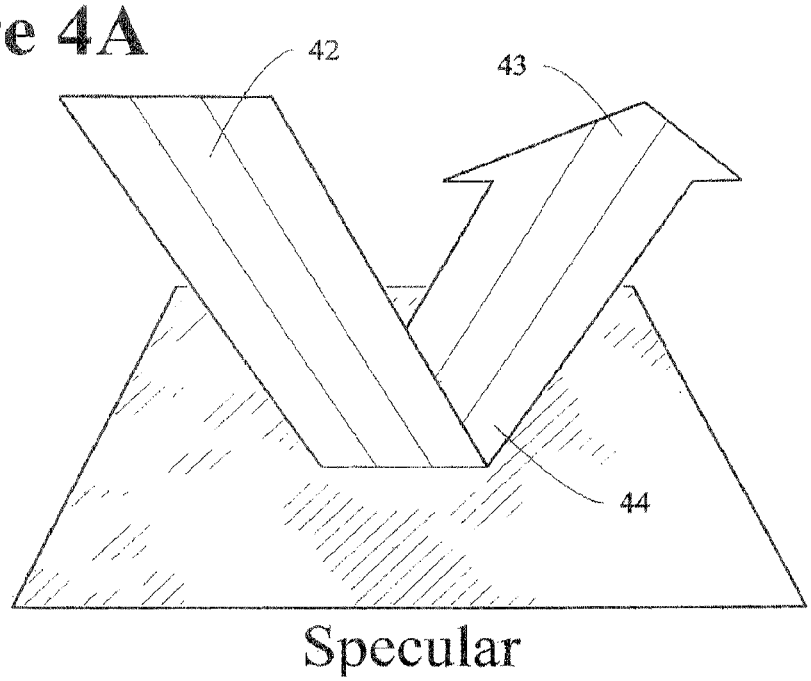
FIG. 4 is a perspective drawing illustrating Specular Reflection versus Diffuse Reflection.
Figure 4B:
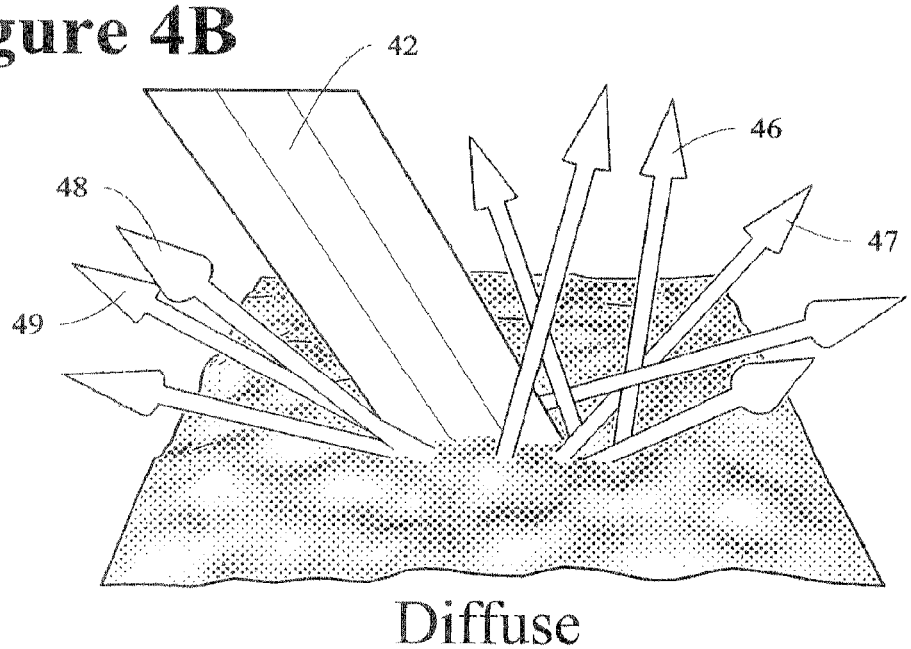

FIG. 4A illustrates specular reflection, in which incident light 42 is reflected from object 41, with essentially all of the resulting reflected light 43 leaving the object at the same angle 44. A camera receiving the reflected light 43 would "see" a patch of glare on the object 41 rather than detailed image information for the object in the area of reflection. FIG. 4B illustrates diffuse reflection, in which incident light 42 is scattered from object 45, resulting in various reflected beams of light such as at 46, 47, 48 and 49. This type of reflection, when viewed by an imaging system, can provide image detail for the object 45. The nature of specular reflection is that from a single illuminator source, the specular reflection off a portion of target can only be captured (undesirably) by one of two cameras that are physically separated along a line above the target on which the illumination source is also aligned.

Figure 5A:
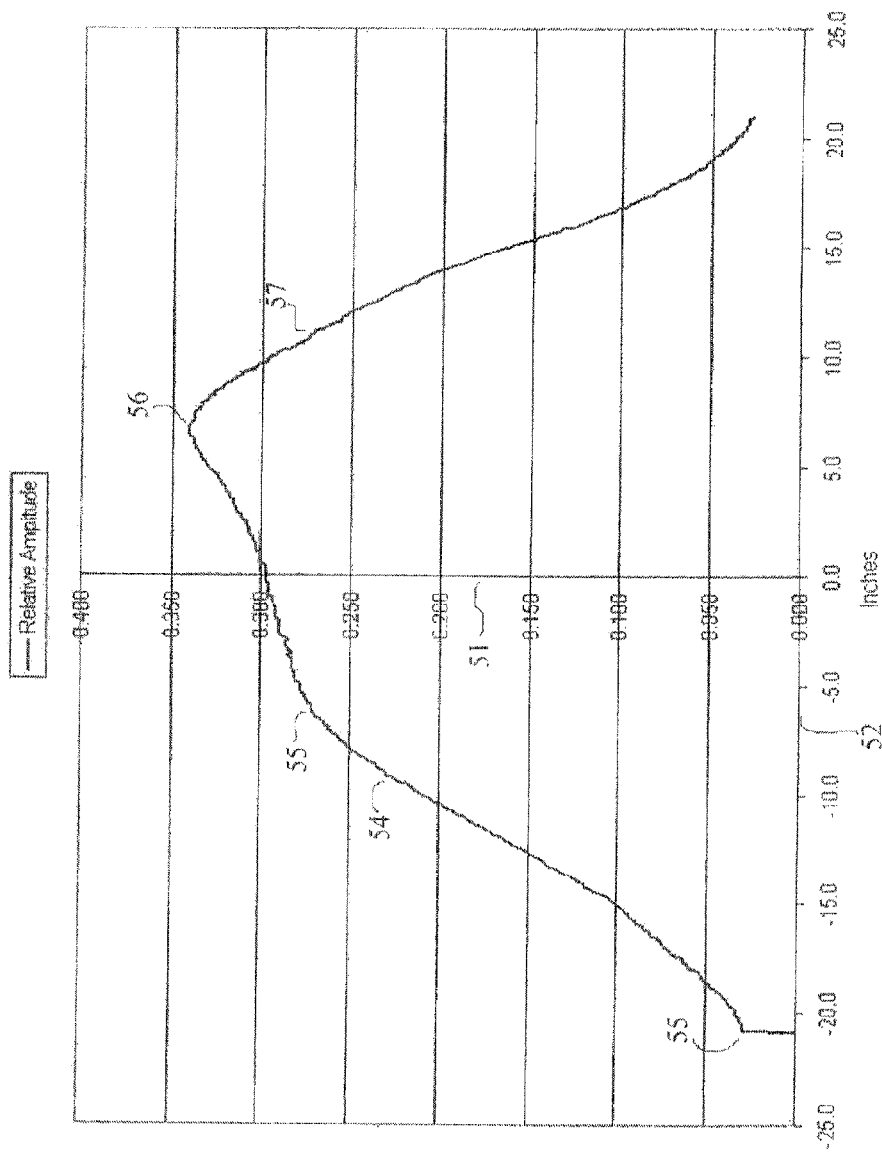
FIG. 5A is a graph of Projector Radiation pattern.

If a point source (or near-point-source) illuminator (such as LED illuminator 32 in FIG. 3) projects light across the scan zone, the resulting Projector Radiation Pattern will vary across the scan zone due to dispersion of light as distance increases and due to structural differences in the light as it proceeds from its source. FIG. 5A shows an example of varying amplitude (along relative Amplitude axis 51) of Projector Radiation Pattern at positions along the graph's Y-axis (which corresponds to the scan zone's horizontal Y-axis in FIG. 2). The radian amplitude by a light sensor is low at position 55, rises rapidly to position 54, continues rising past 55 although less steeply, peaks at 56, and then descends rapidly past position 57. FIG. 5B shows corresponding lines of amplitude response for different heights of the gray card within the scan zone, that is, at different positions (X=24, X=28, and X=32) along the vertical X-axis of FIG. 2.

Figure 6A:
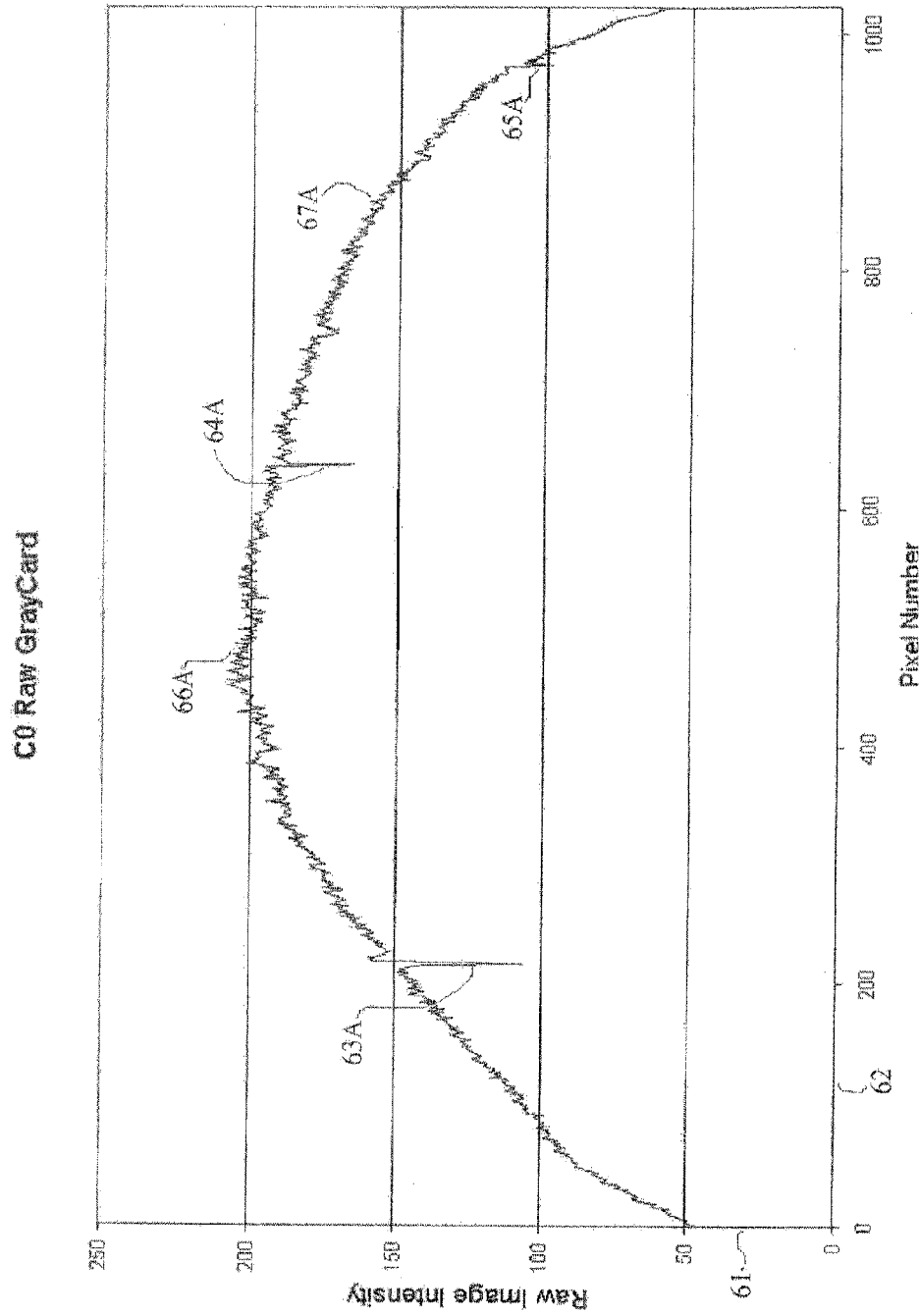
FIG. 6A is a graph of GrayCard Raw Image data from Camera 0, with aberration "dips" that reflect obvious lines on the GrayCard.

FIG. 6A shows a corresponding variation in Raw Image Intensity picked up by Camera 0 when an LED illuminator (32 in FIG. 2) projects light across several adjoined reflective gray cards in the scan zone (22 in FIG. 2). The resulting image pixels of line 67A start off low near Raw Image Intensity axis 61, increasing until there is an aberrant and sudden dip at 63A (which corresponds to the geometric location of a small gap between gray cards in the scan zone), increases again to peak 66A and curves downward slightly to the next aberrant and sudden dip at 64B (which corresponds to the geometric location of another small gap between gray cards in the scan zone), and proceeds downward to a third aberrant and sudden dip at 65A (which corresponds to a third small gap between adjacent gray cards in the scan zone.

Figure 6B:
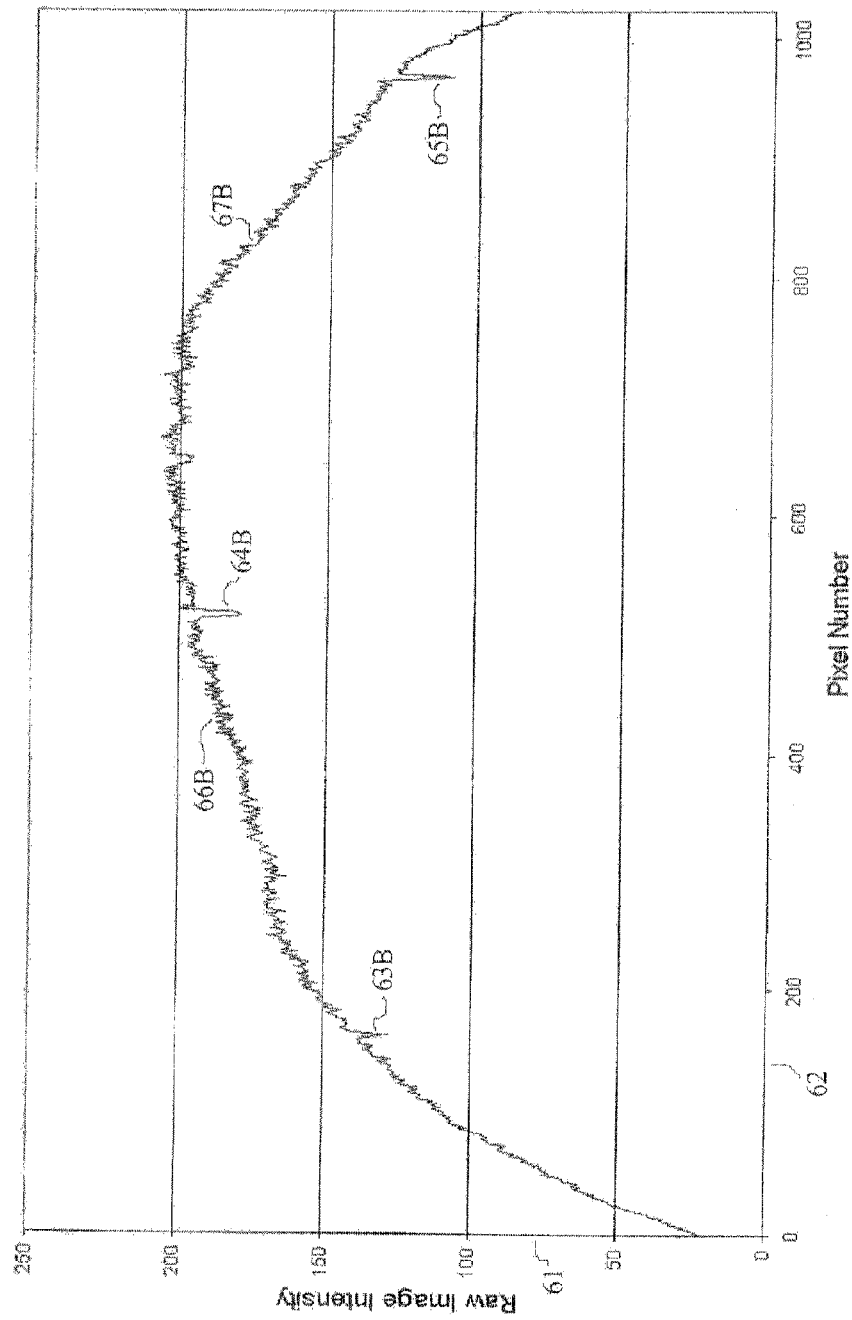
FIG. 6B is a graph of the corresponding GrayCard Raw Image data from Camera 1, showing different aberration "dips" from FIG. 6A.

FIG. 6B shows a comparable Raw Image Intensity line 67B that is picked up by Camera 1, with again, aberrant dips at 63B, 64B, and 65B. Notice however that the positions of those dips (which likewise correspond to small gaps between adjacent gray cards in the scan zone) are at different pixel numbers for Camera 1 than they were for Camera 0 in FIG. 6A—this is a result of the different positions and perspectives of Cameras 0 and 1. Also note that although the peak intensity for Camera 0 in FIG. 6A at 66A came before (to the left of) aberrant dip 64A, a comparable position (such as 66B) past pixel 400 on FIG. 6B has not yet reached the peak intensity seen by Camera 1, which peak occurs at a pixel number (on y-axis 62) that is actually past aberrant dip 64B and past pixel 600 on FIG. 6B. Each of Camera 0 and Camera 1 is recording image data from the same target object—but the image data is different. It still remains to somehow take the best of each set of image data for eventual use.

Figure 7A:
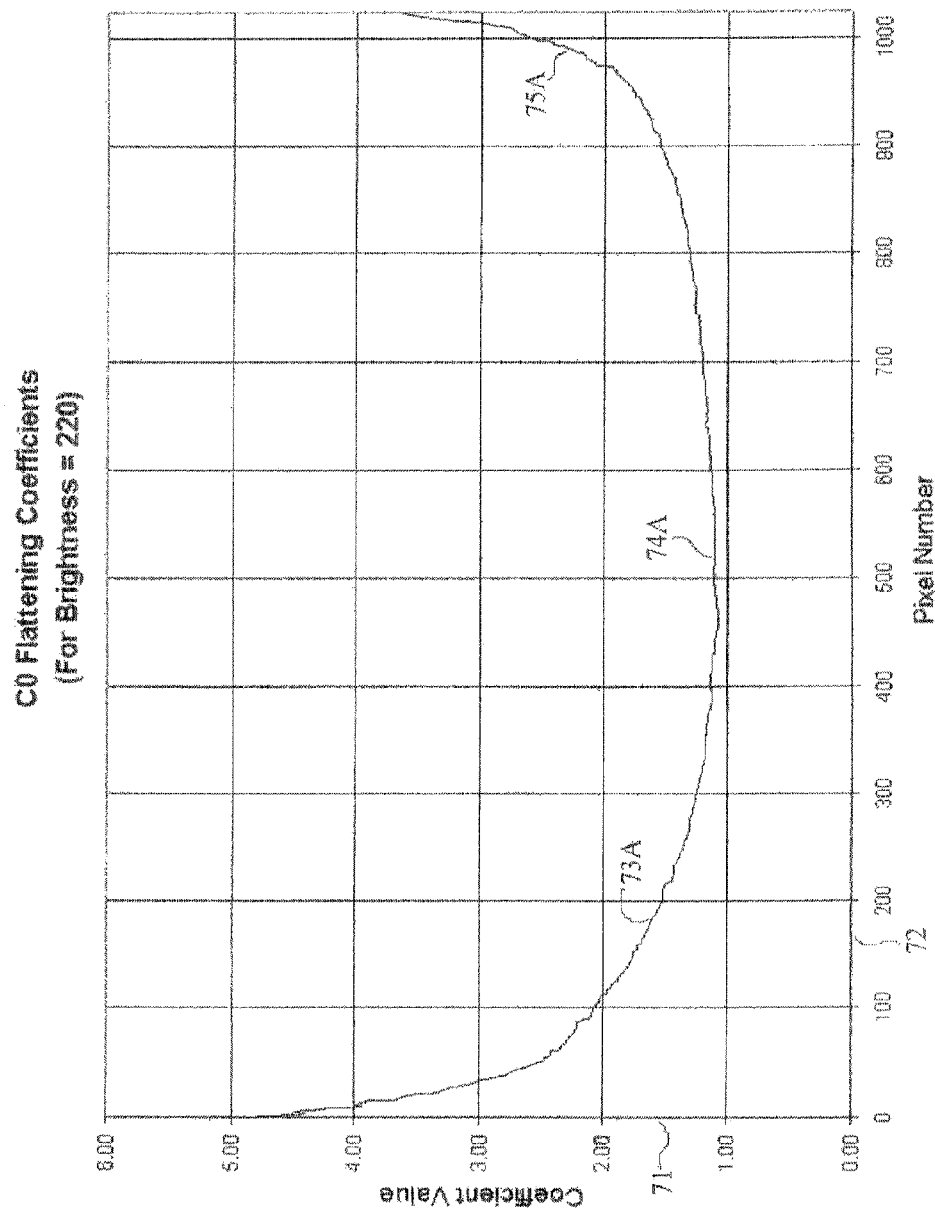
FIG. 7A is a graph showing the calculated Flattening Coefficients for Camera 0.

The results shown in FIGS. 6A and 6B are then used to obtain Flattening Coefficients (e.g. for an illuminator Brightness of 220) for each of Camera 0 and Camera 1, as shown in FIGS. 7A and 7B. In their bracketed subtitle "For Brightness=220", the "220" refers to the level on a brightness scale ranging from 1-256. In both FIGS. 7A and 7B, the required Flattening Coefficient value starts off high at low Pixel Numbers on axis 72, gradually diminishes past points 73A (FIG. 7A, for Camera 0) and 73B (FIG. 7B, for Camera 1), bottoming at 74A and 74B respectively, and rising again past 75A and 75 B respectively. Interpolations are used in place of the aberrant dips from FIGS. 6A and 6B respectively to obtain the Flattening Coefficients for the pixels of each of Cameras 1 and 2 across the scan zone.

In the "Flattening" method, a sample target of known, essentially uniform diffuse reflective properties is imaged at a known distance, while being illuminated by each respective illumination source and camera to be used in the system. A "Nominal Flat" signal level is selected (considering minimum and maximum Raw signal amplitudes and dynamic range of downstream processing). Coefficients for each pixel in the imaging system are determined, such that each pixel's coefficient, when multiplied by the amplitude of its corresponding Raw image pixel amplitude, will render a Nominal Flat pixel amplitude value (as near as quantization and other noise sources allow) linearly correlatable to the known reflective properties of the target. Following flattening, images from both cameras are considered normalized on a reflectivity response basis.

Figure 8:
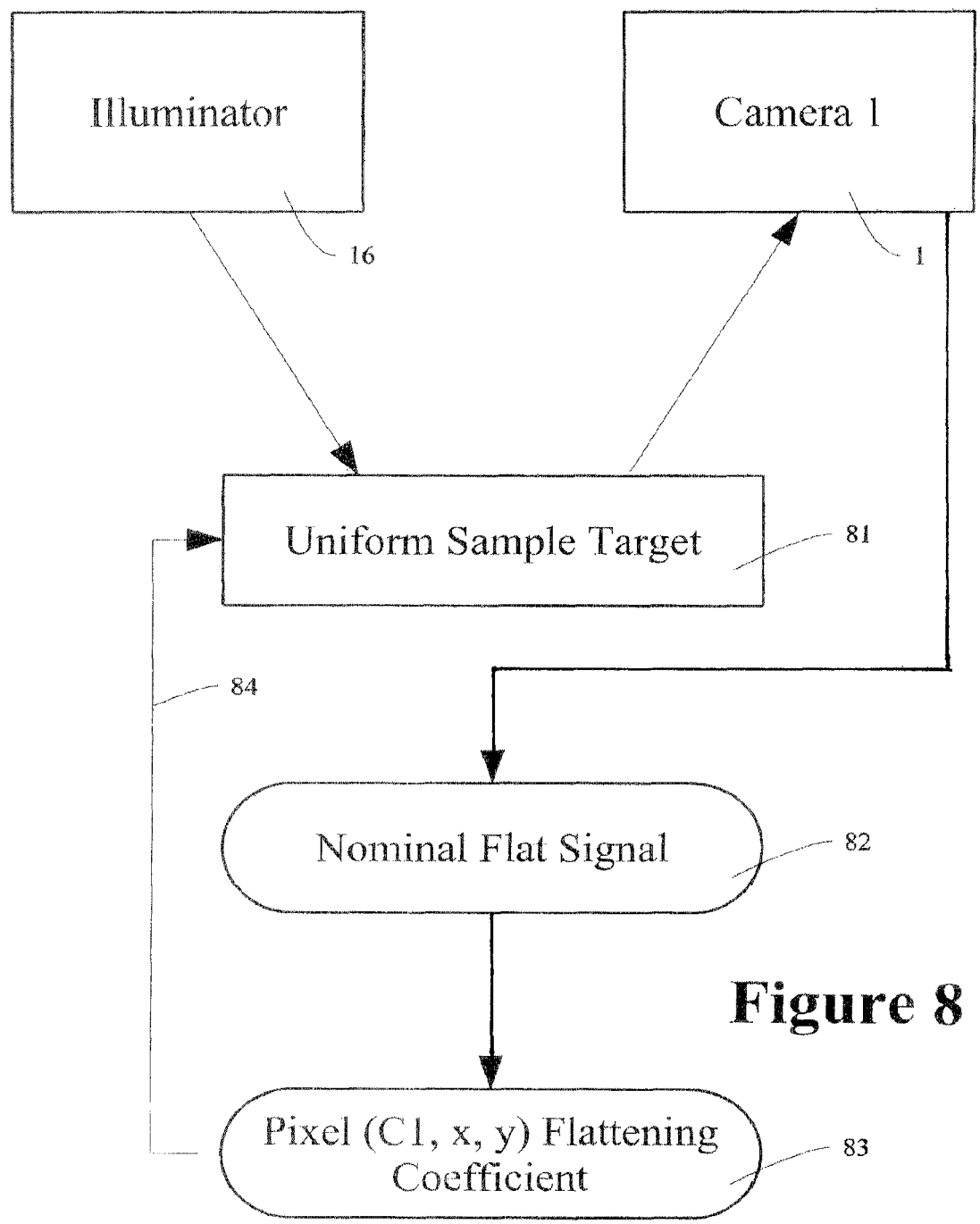
FIG. 8 is a block diagram showing the obtaining of Flattening Coefficients for later use in the Flattening subprocess.

Saving the Flattening Coefficients for all pixel numbers for each Camera reflected from the scan zone enables the processing of Raw Image Data from each Camera into Flattened Image Data from each Camera. FIG. 8 shows the method and apparatus to be used: the illuminator 16 projects light onto a uniform sample target 81, camera 1 records a nominal flat signal 82 for a first Pixel at coordinates x and y in a plane in the scan zone and a Flattening Coefficient 83 is derived for that Pixel. The process is repeated in a loop 84 until a table of Flattening Coefficients is built up for all relevant pixel positions to get, for example, a brightness level of 220 out of a maximal 256 for that camera.

FIG. 9 is a spreadsheet table for successive pixels assembled with Raw Data column 91 and Camera 1 GrayCard Flattening Coefficients column 92, taken at 24 inches between the scan head and the target. The table proceeds with Target Flattened Column 93 and Ortho Target Column 94 that reflect the Gridizing process, which turns Flattened Data for a pixel into Ortho data for the same camera. A family of co-efficients thus derived (for example, every potentially applicable ¼ inch between the scan head and the target). The applicable Flattening Coefficient can then be applied to each line of raw data such as shown in FIG. 6.

Once both the data from Camera 0 and the data from Camera 1 are processed into Ortho 0 and Ortho 1 data via the Gridizing process, the respective sets of data from Camera 0 (C0) and Camera 1 (C1) can then and only then be compared on a pixel (C0,x,y) by pixel (C1,x,y) basis, where each corresponds to the same pixel-area on the target object itself.

Figure 10B:
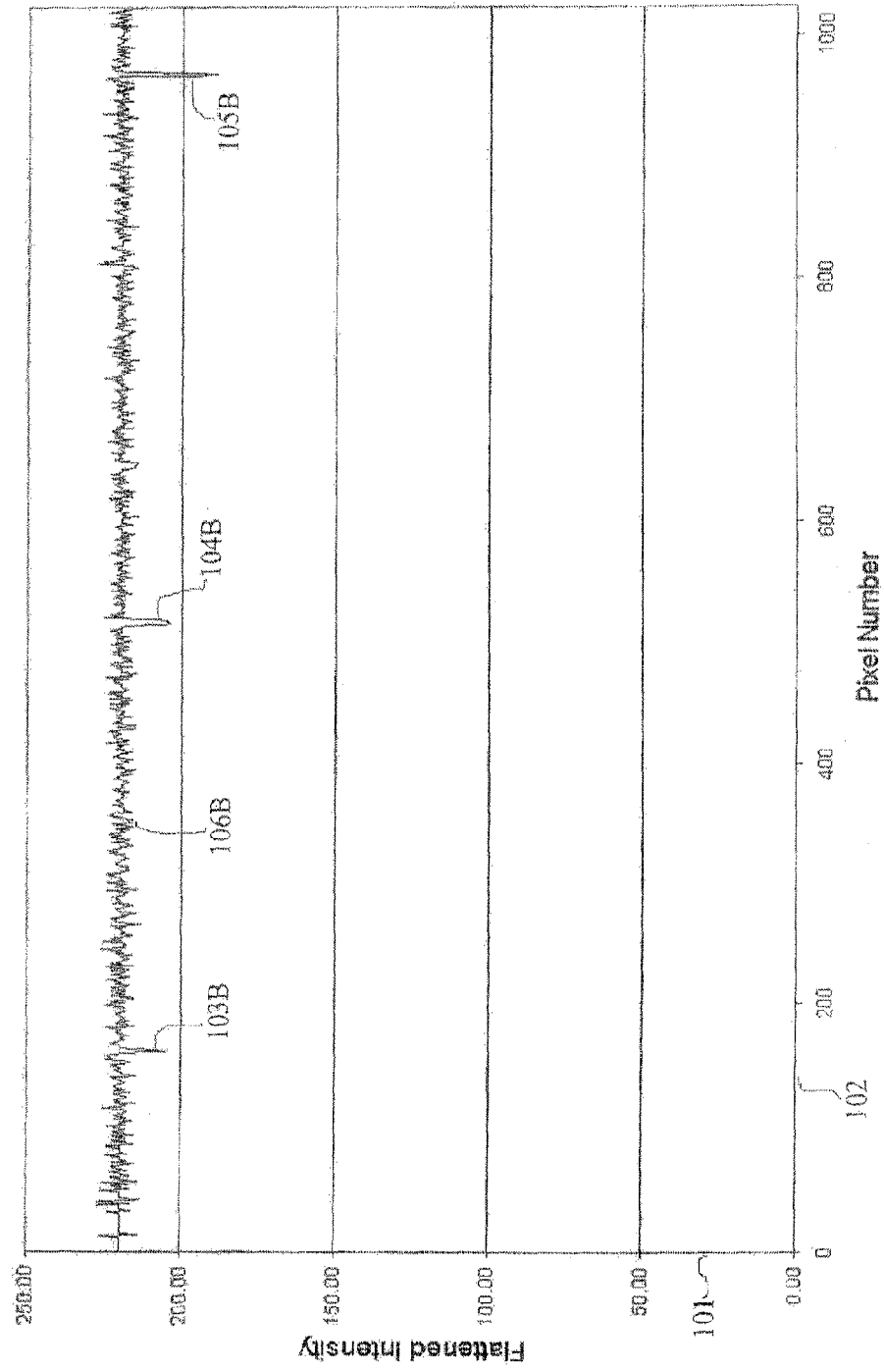
FIG. 10B is a graph of Flattened Image data from Camera 1.

FIG. 10A illustrates the result of applying the Flattening coefficients to Camera 0's Graycard Target Image data. For Pixel Numbers along axis 102, the Flattened Intensity along axis 101 is slightly variable along line 106A, with the exceptions of aberrant dips 103A, 104A, and 105A, which still represent the small gaps between adjacent gray cards. Likewise in FIG. 10B, the Flattened Graycard Target for Camera 1 is shown, with the aberrant dips 103B, 104B, and 105B along 106B also representing the same small gaps between adjacent gray cards in the target scan zone, but being at different pixel numbers for Camera 1 (in FIG. 10B) than the aberrant dips were for Camera 0 (in FIG. 10A). The effect of parallax can still be seen in the different locations of the corresponding aberrant dips as between FIGS. 10A and 10B.

Figure 11:
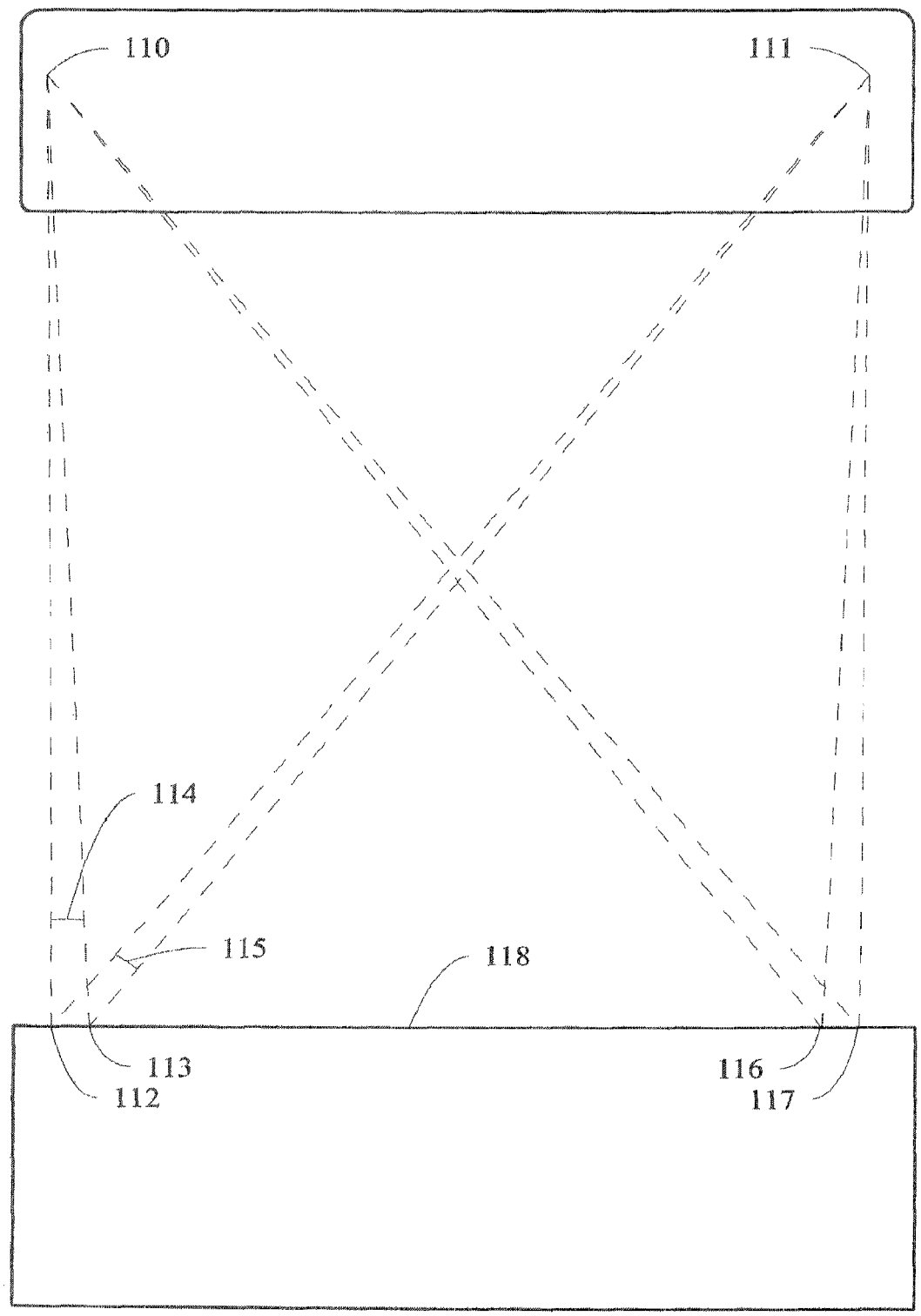
FIG. 11 shows the problem of parallax in using two separated cameras to view the same area of a target surface.

FIG. 11 shows the problem of parallax in attempting to compare pixel data from one camera with pixel data from another camera, where the objective is to obtain an enhanced image of the same area on a target using image data from both cameras. The surface line between points 112 and 113 on a scan zone target object 118 can be seen by a camera at scan head location 110 with pixels along line 114 on a nominal 1:1 basis. However, a second camera at scan head location 111 sees the same surface line between points 112 and 113 with a narrower set of pixels, along line 115. The two perspectives' parallax is reversed for the surface line between points 116 and 117 on the target object 118. The effect is that pixels from either camera are covering more territory on the target with each pixel farther out than a camera pixel covering an area on the target object directly below the camera. An orthographic perspective is one taken as if with a camera at an infinite distance away from the target.

Figure 12A:
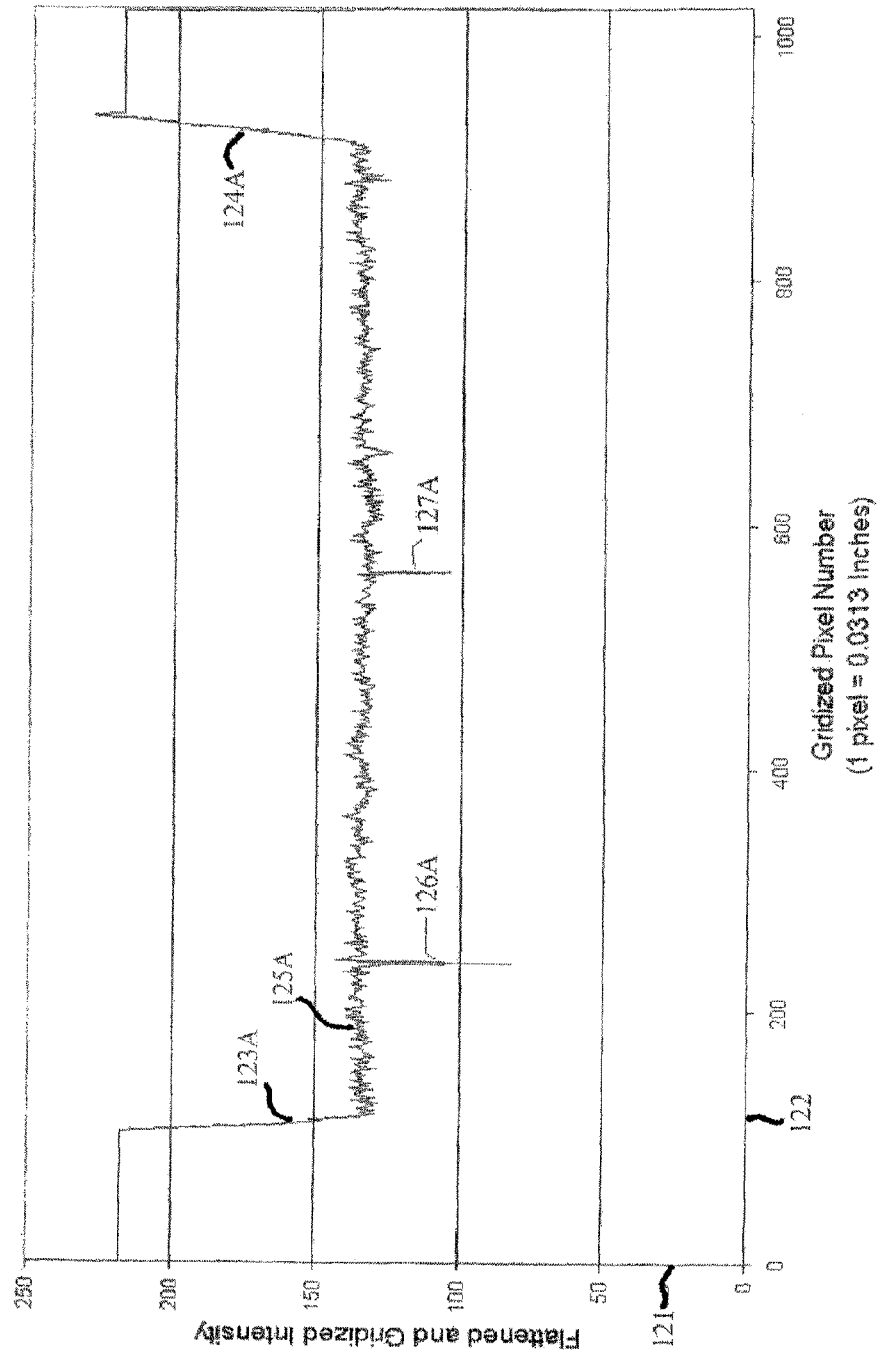
FIG. 12A is a graph of Ortho Image data (i.e. Flattened and Gridized) from Camera 0, from a target GrayCard.
Figure 12B:
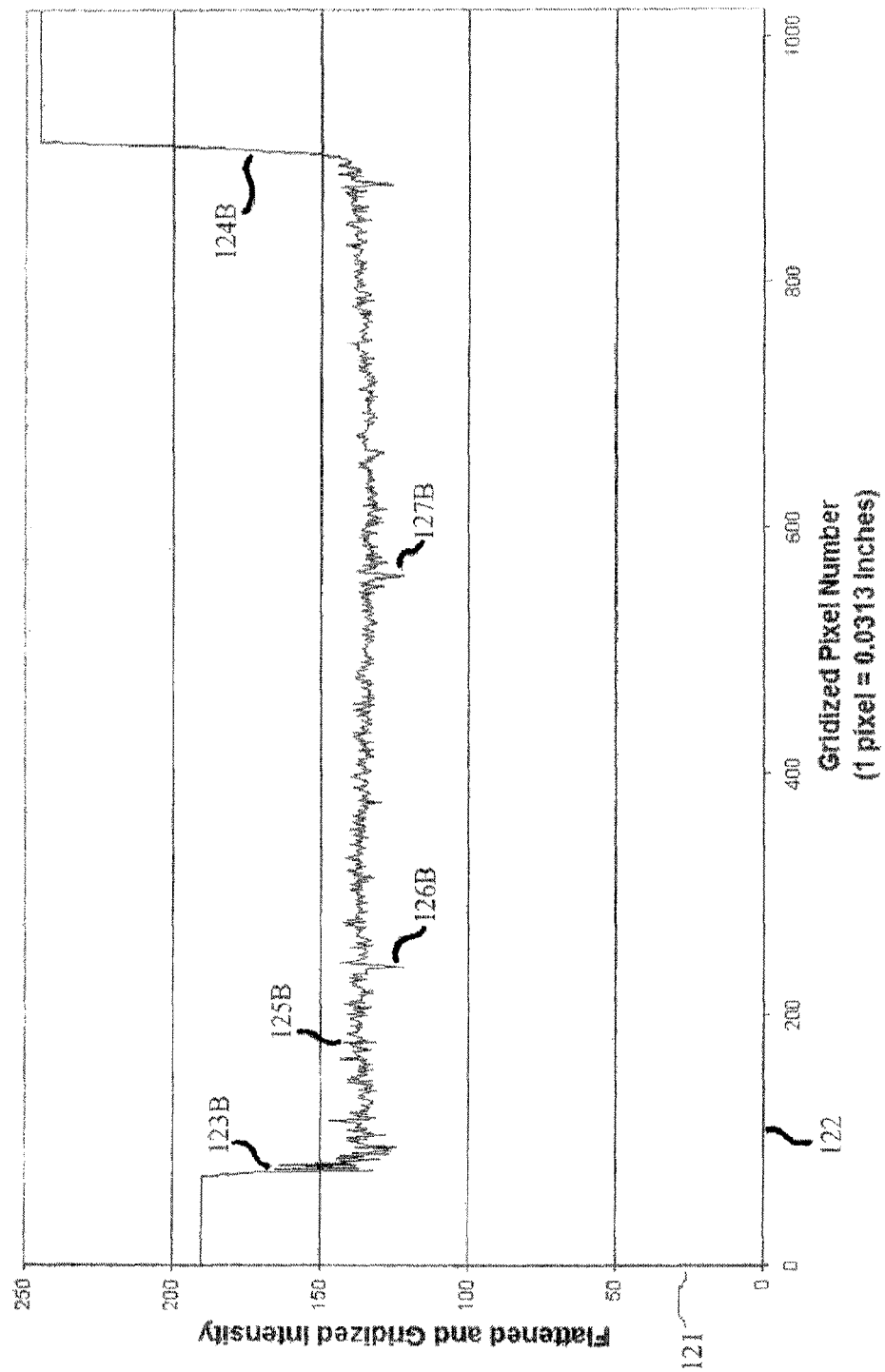
FIG. 12B is graph of Ortho Image data (i.e. Flattened and Gridized) from Camera 1, from a target GrayCard.

FIG. 12A shows a graph of Flattened and Gridized Intensity axis 121 for Gridized Pixels axis 122 for Camera 0's view of the Graycard. The Gridizing corrects for parallax for Camera 1 by moving its image data from FIG. 10A an increasing fraction of a pixel over as its parallax increases along the corresponding target surface. The Flattened and Gridized Intensity line 125A data ceases relevance at 123A on the left and 124A on the right. In between, the aberrant dips at 126A and 127A can still be seen, reflecting the graycard small gaps. FIG. 12B shows the corresponding Flattened and Gridized Intensity data for Camera 1. It will be noticed that the left and right irrelevance boundaries 123B and 124B in FIG. 12B now align with the corresponding 123A on the left and 124A on the right in FIG. 12B. Similarly, the aberrant dips 126B and 127B in FIG. 12B now align with the corresponding dips 126A and 127A in FIG. 12A. The lines 125A and 126B are not identical. They are however, now meaningfully comparable on a pixel-by-pixel basis. Each value for intensity for a given Gridized Pixel Number on FIG. 12A (Camera 0) can be compared to the corresponding Gridized Pixel Number on FIG. 12B (Camera 1), because each now represents the same location on the target object.

Figure 13:
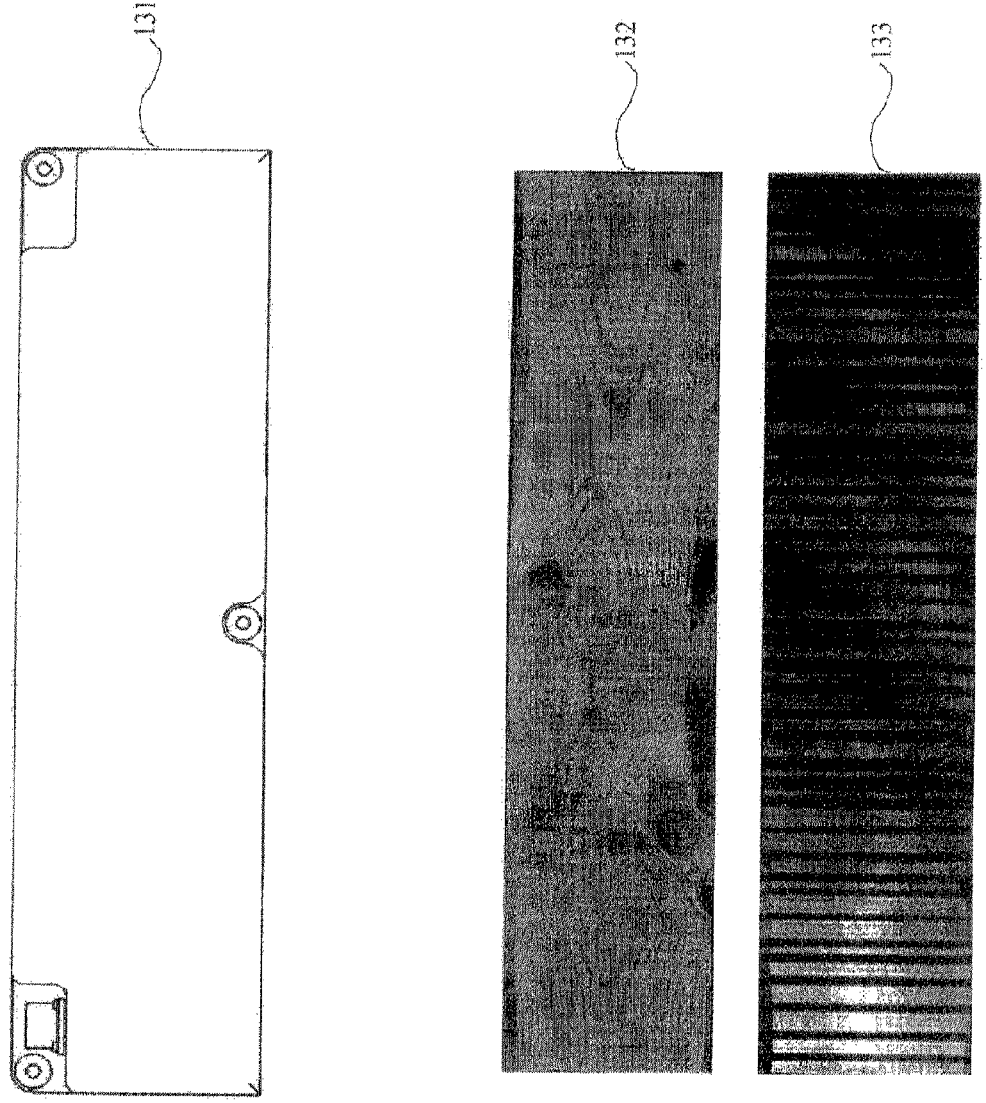
FIG. 13 is a front view of a scan head containing Camera 0, Camera 1, and an illuminator, a length of lumber, and bars of coded light.

FIG. 13 shows a scan head 131, a board of lumber 132, a coded light pattern 133 emitted by a laser. When the lumber 132 is passed through a scanning pattern of bars of coded light, the reflection back to a camera from the lumber will show information in the reflected light from which a geometric shape of the lumber can be calculated. The geometric shape can be mapped with coordinates. U.S. Pat. No. 5,615,003 (Electromagnetic profile scanner) and U.S. Pat. No. 5,986,745 (co-planar electromagnetic profile scanner) show in detail a system for determining the shape and dimensions of a surface of an object includes a projector for projecting onto the object a spatially coded pattern of radiation, for example, laser light. That system also includes a receiving device capable of imaging the reflected pattern, and a discriminator for determining which portion of the reflected pattern corresponds to which portion of the projected pattern. By this means, a received signal representing less than the complete reflection from the projected pattern can be correlated with a discrete portion of the scanned object. The procedure is repeated to obtain enough reliable data to generate a reasonably reliable surface profile. The resulting set of received signals and correlations are used to calculate the shape and dimensions (geometric profile) of the object.

The surface appearance of lumber and other objects gives useful information, over and above its mere geometric profile, as to the lumber's characteristics. For example, knots are of paramount concern in finished lumber. Besides being either aesthetically desirable or undesirable for a particular application, wood knots present a structural problem, although they would not show well or at all in a mere geometric profile of a board of lumber (except to the extent the knots corresponded exactly with ridges or depressions in the geometric profile). Often a surface on a board of lumber is smooth enough that knots, while present and visible, do not show well or at all in a geometric profile of the board. Knots are tougher to saw than un-knotted wood, yet define areas of weakness in lumber along which it is likely to crack. It is generally preferable to have a knot embedded in a piece of finished lumber than to have it on a surface or an edge.

Figure 14A:
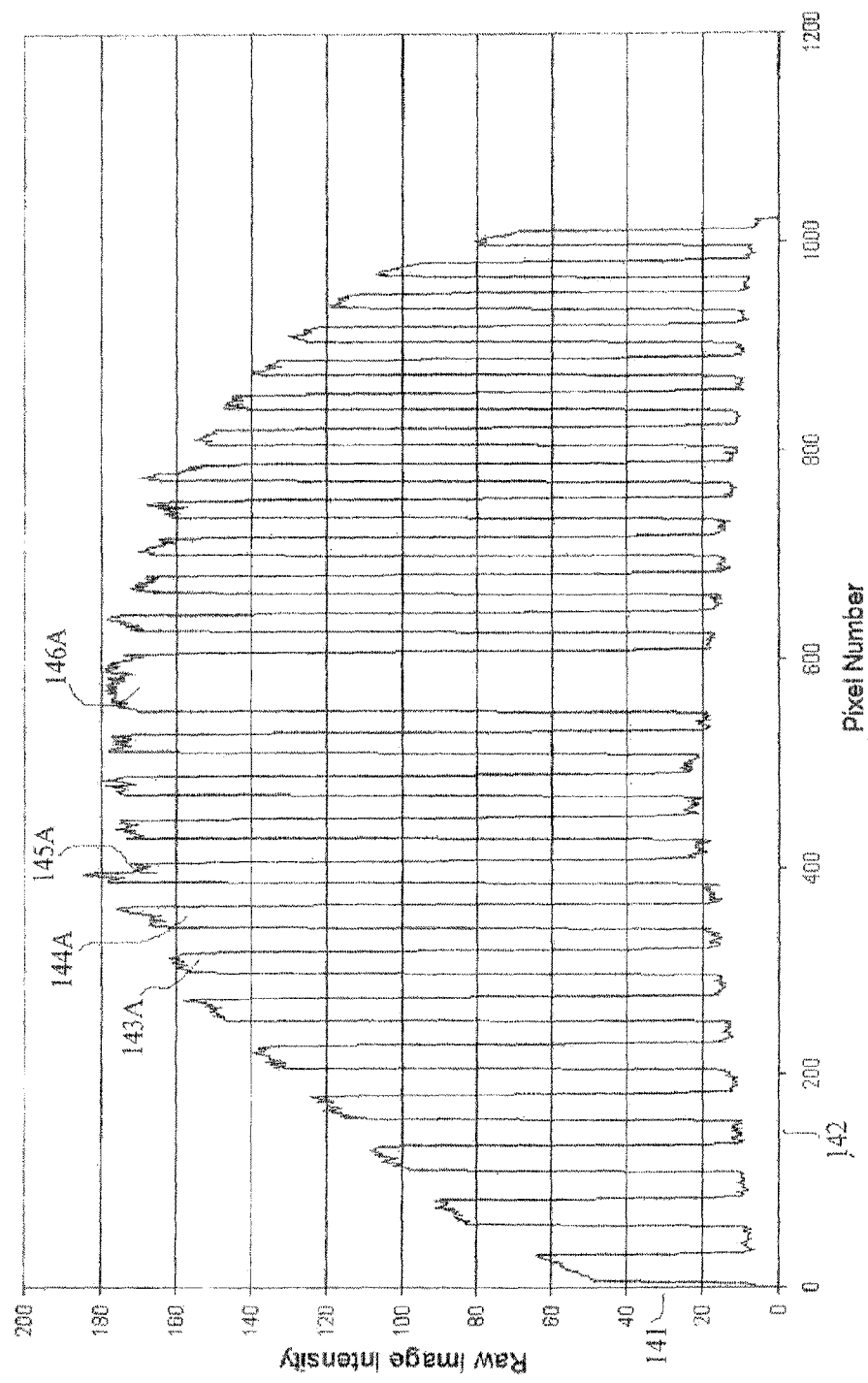
FIG. 14A is a graph of Raw Image data from a striped target, from Camera 0, showing an middle aberration on the striped target.
Figure 14B:
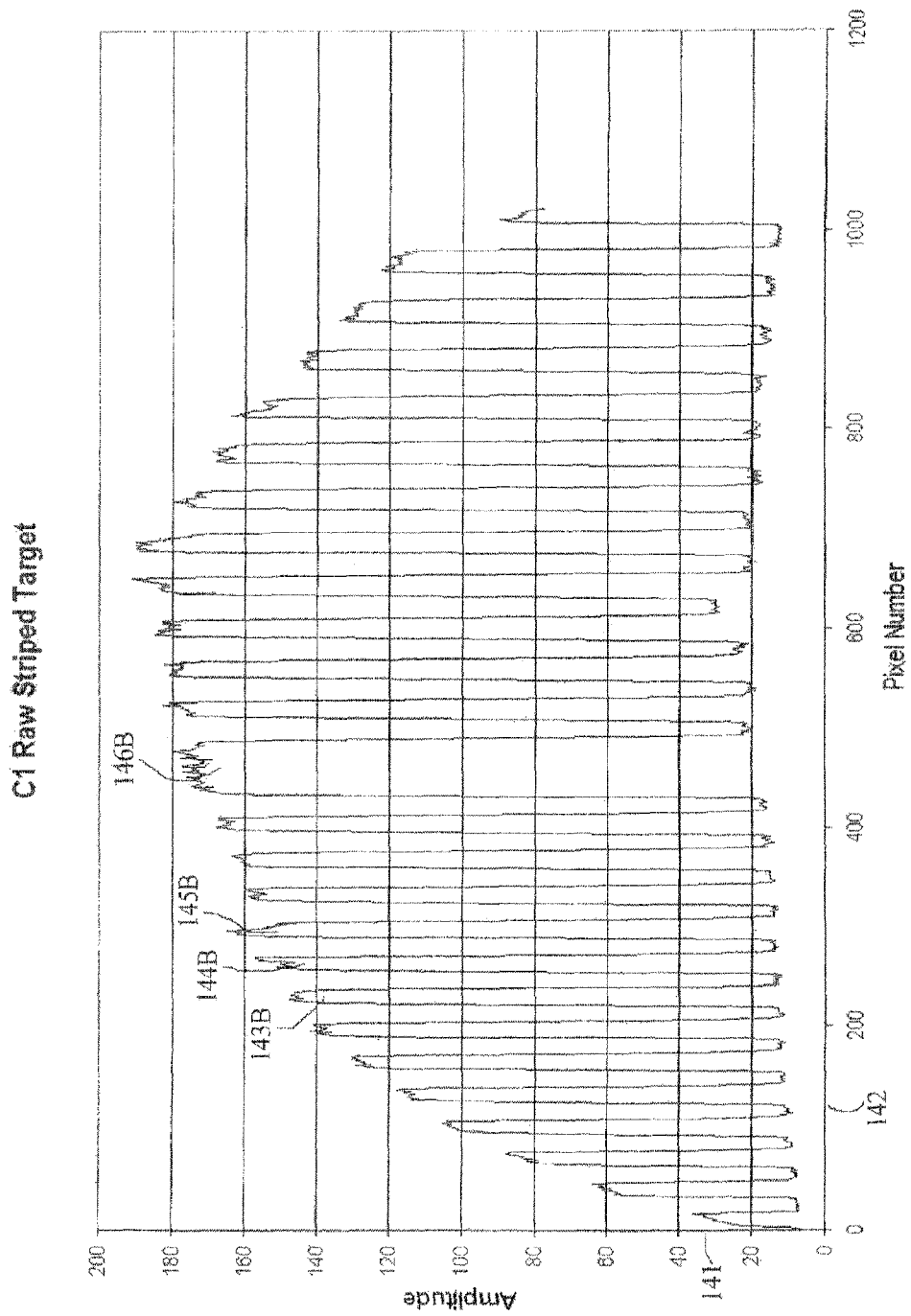
FIG. 14B is a graph of Raw Image data from the striped target, from Camera 1, showing a different placement of the middle aberration on the striped target from FIG. 14A.

FIG. 14A shows a Raw Image Intensity axis 141, pixel Number axis 142, a graph of Raw Image data from Camera 0 of a striped target. A surface aberration 146A is apparent. Notice also the shape of the high intensity bars at 143A, 144A, and 145A. They correspond to the surface aberration 146B, and the high intensity bars 143A, 144B, and 145B in FIG. 14B, although the those features are at different pixel numbers in FIGS. 14A and 14B.

Figure 15A:
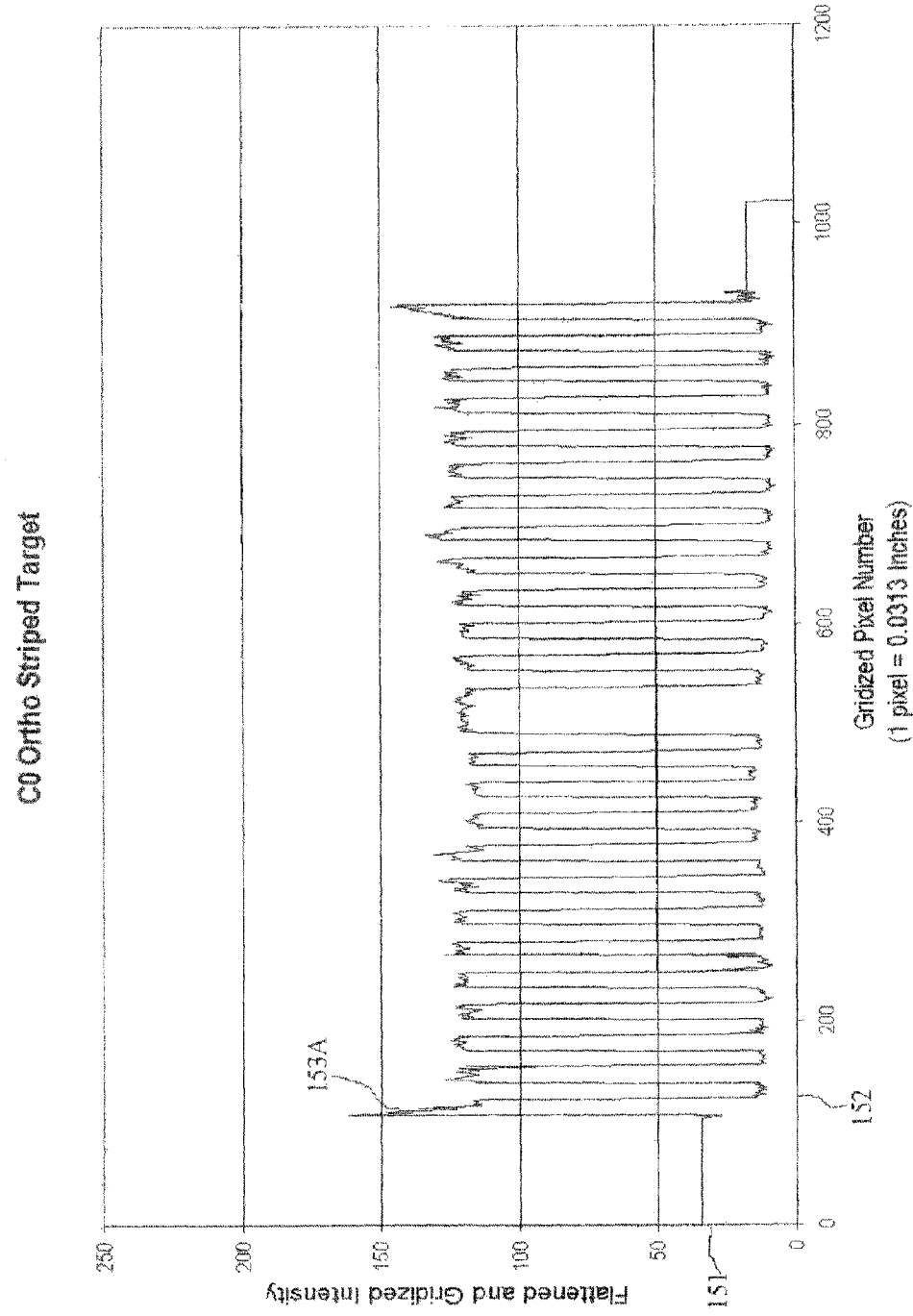
FIG. 15A is a graph of Ortho Image data from the striped target, from Camera 0, after Gridizing.
Figure 15B:
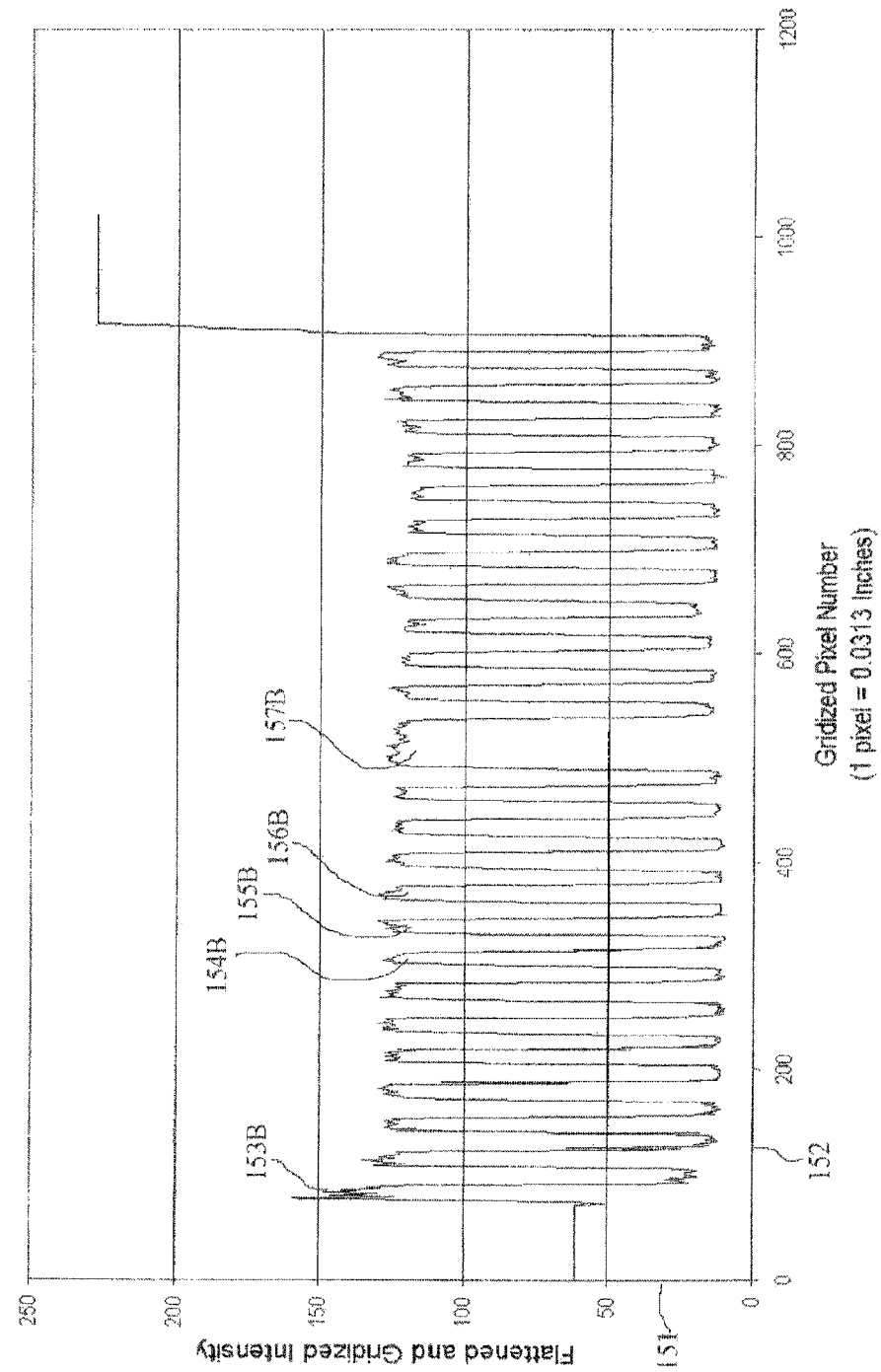
FIG. 15B is a graph of Ortho Image data from the striped target, from Camera 1, after Gridizing, showing the middle aberration from the striped target is now aligned along the horizontal axis the same as in FIG. 15A.

FIGS. 15A and 15B show the same data, but Flattened and Gridized for Camera 0 and Camera 1 respectively. Once past the irrelevance marker of high intensity at 153A and 153B, the data is generally flat in response at both the upper (highly lit and reflective) and lower (dark and non-reflective) ends of the bars. The detailed shape of the bars at 154A, 155A, 156A is somewhat similar to the corresponding features at 154B, 155B, and 156B. The main point is that the vertical Flattened and Gridized Intensity axis 151 data at those points can be compared between Camera 0 and Camera 1 because both sets of data are now aligned along the horizontal Gridized Pixel Number axis 152. The aberration represented by Flattened and Gridized image data at 157A and 158B is of particular interest because the details of intensity vary so much in that area depending on perspective. In such an area of interest, the determination of which pixel of intensity as between Camera 0 and Camera 1 provides the most informative data for an enhanced image is best illustrated by actual images of actual lumber.

Figure 16A:
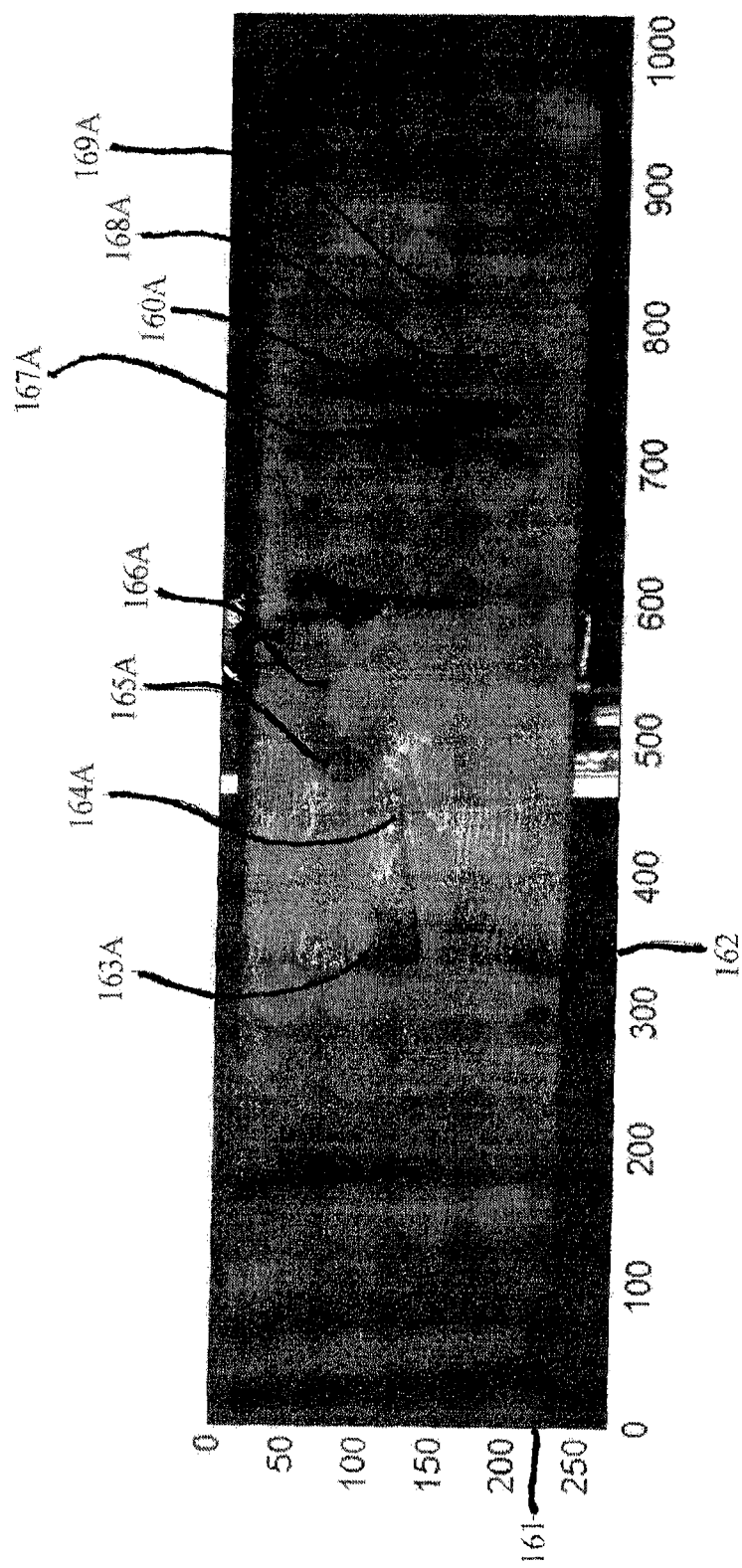
FIG. 16A is an actual image from Raw Image data from Camera 0, showing an area of specular reflection in the middle area of target object board, and an indication of other aberrations in the board to the right.
Figure 16B:
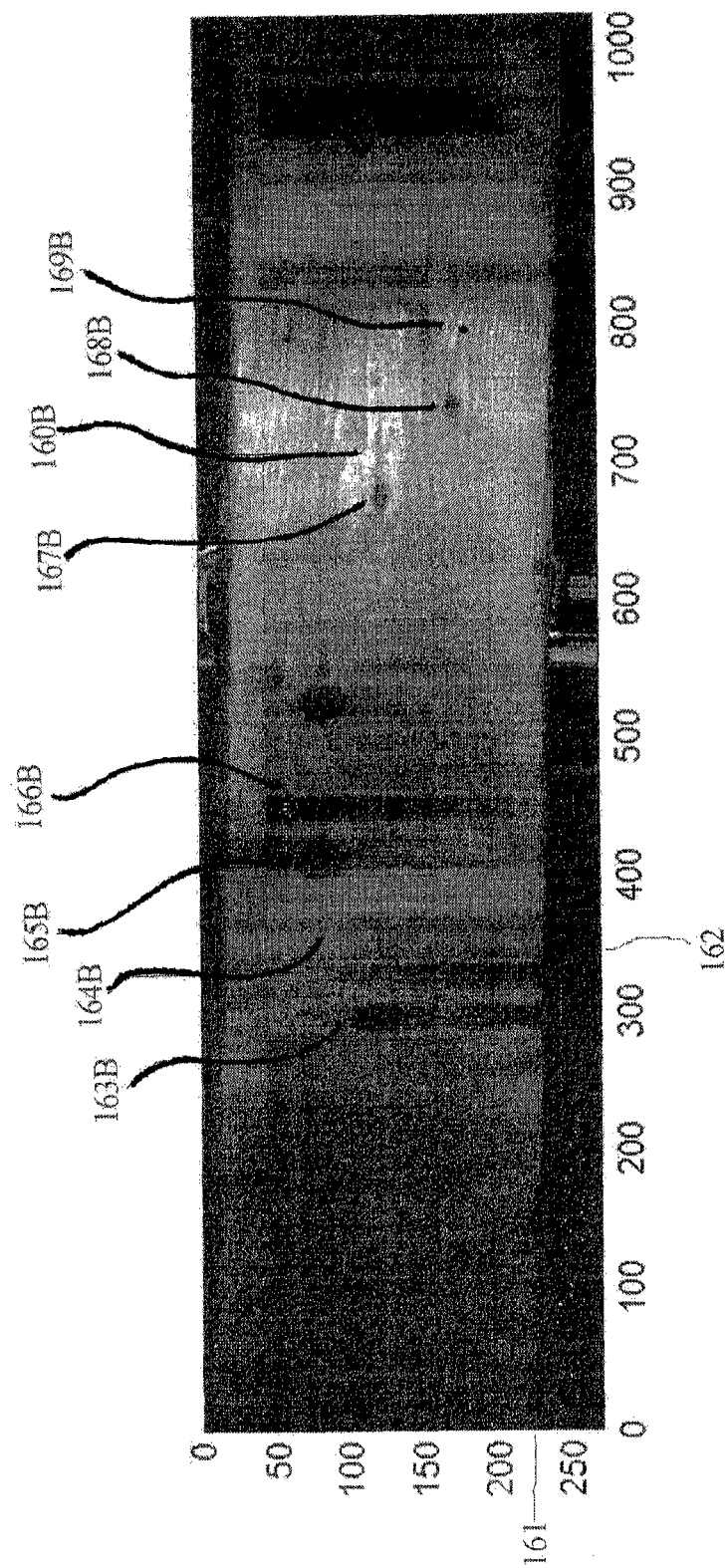
FIG. 16B is an actual image from Raw Image data from Camera 1, showing an different area of specular reflection, nearer to the right side of the same target object board, and an indication of an aberration in the center of the board corresponding to the area specular reflection in FIG. 16A.

FIG. 16A shows a Raw Image from Camera 0 of a board of lumber on which there is a first selected large knot 163A, an area of specular reflection 164A, a second selected large knot 165A, a first selected small knot 166A, a second selected small knot 167A, an area 160A without specular reflection, a third selected small knot 168A, and fourth selected small knot. FIG. 16B shows the same board of lumber passing through the scan zone but its Raw Image, taken at the same time, is from Camera 1. Both FIGS. 16A and 16B are mapped onto a pixel number axis 162 (corresponding to Y-axis 26 in FIG. 2) and scan number axis 161 (from the array of linear scans accumulated for each y-axis scan. In FIG. 16B, the image of the first selected large knot (163A in FIG. 16A) is labeled 163B, and so on for the corresponding second selected large knot 165B, the first selected small knot 166B, the second selected small knot 167B, the third selected small knot 168B, and the fourth selected small knot 169B. In FIG. 16B, the area of specular reflection at 160B is in a completely different area on the same board than the specular reflection at 164A in FIG. 16A. The different areas of specular reflection in the images of the board of FIGS. 16A and 16B result in peculiarities of bright image data that is problematic when attempting to compare image point data over the entire board in order to read accurately actual surface anomalies.

Referring to FIGS. 16A and 16B, both raw images are generated by combining a successive number of linear scans of a section of a board. The linear scans from each camera were acquired simultaneously. Three key distortions can be observed in these images:

1) Parallax—in the pixel dimension. A feature (knot 163A) is observed in FIG. 16A at approximately scan number 125, and pixel number 350, while the same feature (knot 163B) appears in FIG. 16B at the same scan number 125 but pixel number 300.

2) Specular Reflection of light source—In the Raw Image of Camera 0, one can see brighter amplitudes from approx. pixels 350 to 600 due to the specular component of reflection from the target. The same applies to the Raw Image acquired by Camera 1 from approx. pixels 550 to 800. Note, and this is key, specular reflection will not originate from the same location on the target in both images, due to geometric displacement of the cameras with respect the illumination source. Specular reflection is that light for which the light rays from the illumination source have equal but opposite angles of incidence and reflection from the target.

3) Variations due to the Radiation pattern of the illumination source and responsiveness of the cameras along the pixel number axis.

Figure 17A:
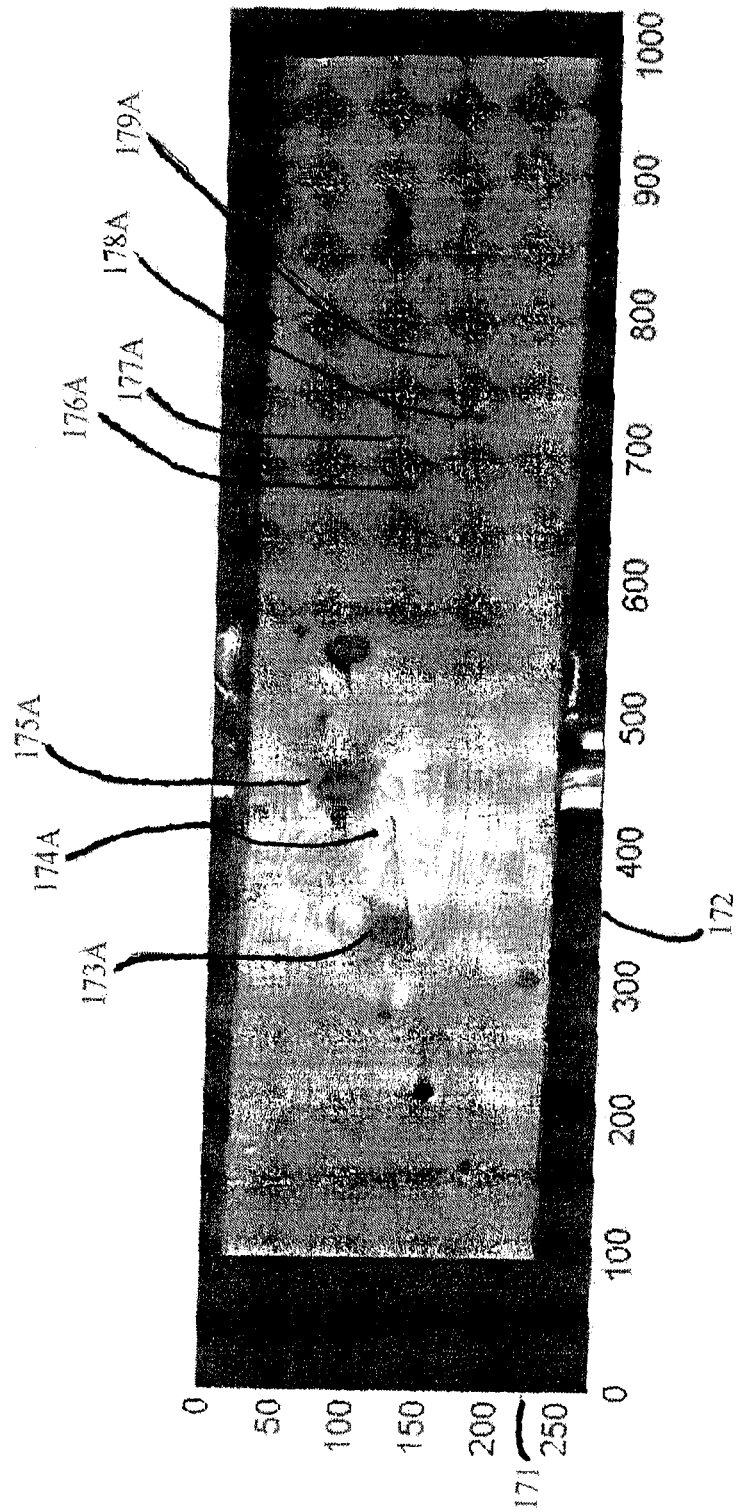
FIG. 17A is an actual image from Ortho (Flattened and Gridized) Image data from Camera 0.
Figure 17B:
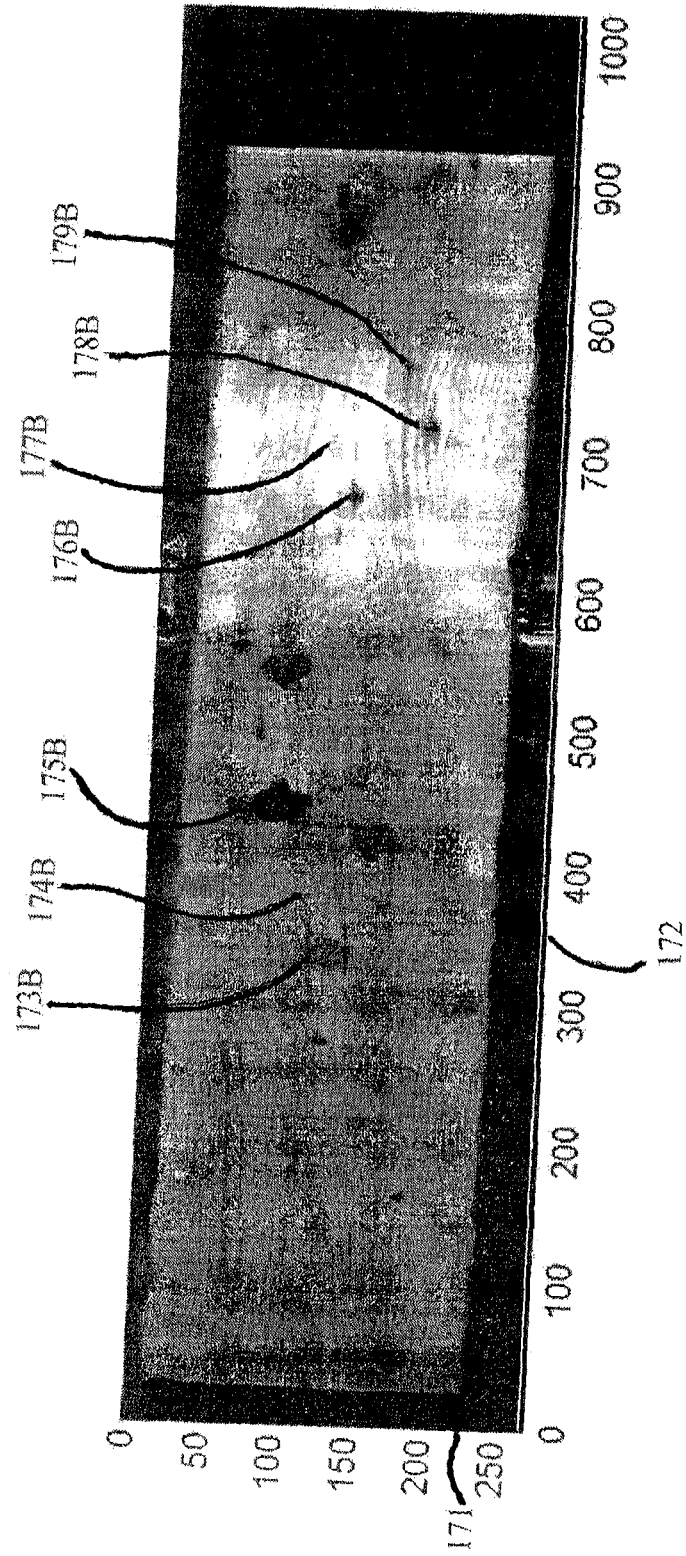
FIG. 17B is an actual image from Ortho (Flattened and Gridized) Image data from Camera

FIG. 17A shows the Flattened and Gridized (IE. Ortho) image from Camera 0, derived by the method and apparatus of the present invention from the Raw Image Data illustrated with the same board in FIG. 16A. FIG. 17B shows the Flattened and Gridized, IE. Ortho, image from Camera 1, derived by the method and apparatus of the present invention from the Raw Image Data illustrated with the same board in FIG. 16B. The pixel number 172 and the scan number axis 171 give coordinates for the lumber at the moment of imaging that are provided via the position encoder 18 and computer control 19 of FIG. 1. Because these coordinates and both images have been Gridized to Ortho Images, the first selected large knot at 173A and 173B, the second selected large knot at 175A and 175B, the second selected small knot at 176A and 176B, the third selected small knot at 178A and 178B, and the third selected small knot at 179A and 179B can both be aligned visually and be compared by a computer on a pixel-by-pixel coordinate basis. The areas of specular reflection 174A and 177B (compare the corresponding areas without specular reflection 174B and 177A) are obviously at quite separate areas on the same board.

Figure 18:
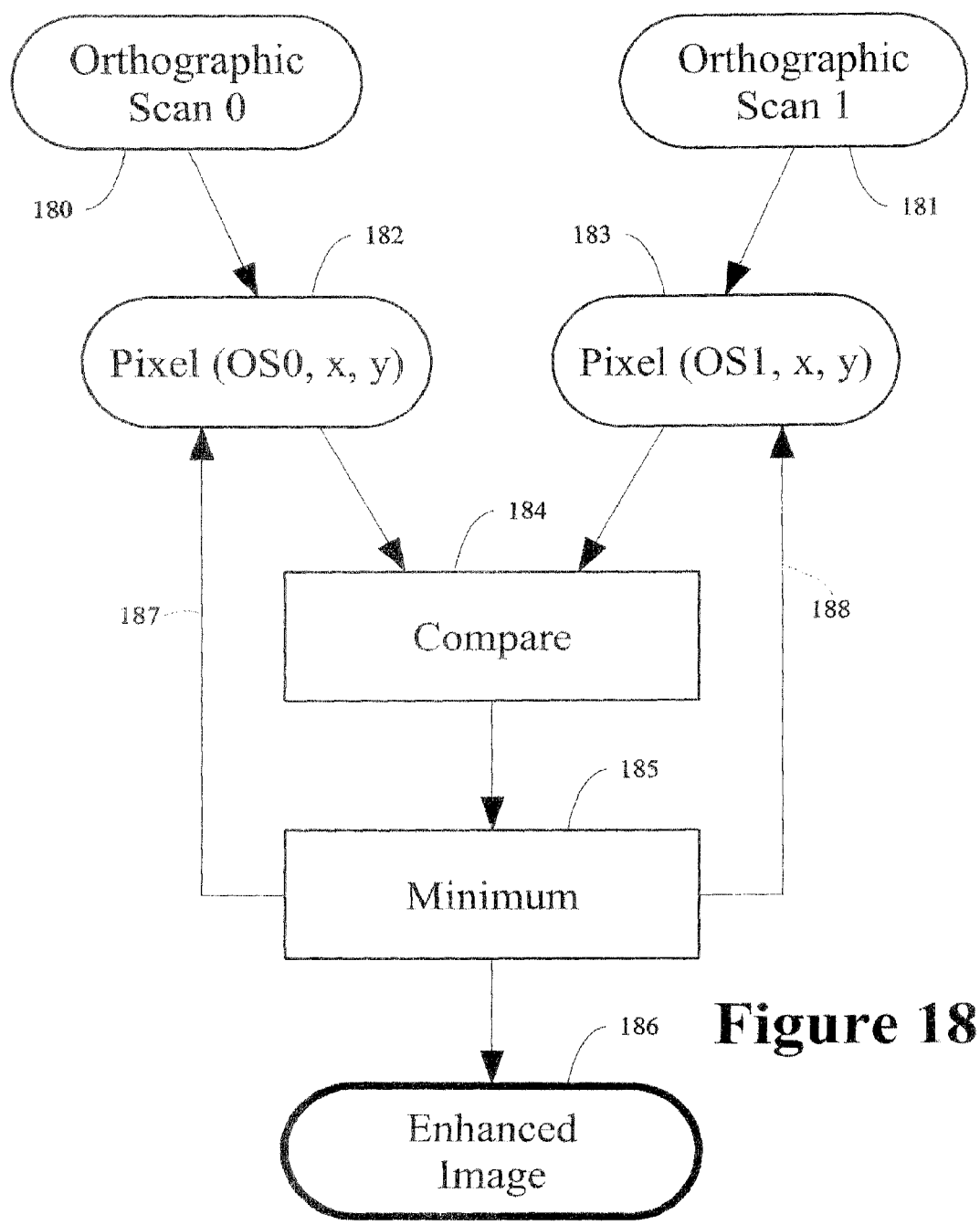
FIG. 18 is a block diagram showing the Selective Combining from Ortho Imaga data from Camera 0 and from Ortho Image data from Camera 1, to result in an Enhanced Image.

FIG. 18 shows the method and apparatus of arriving at an Enhanced image from Ortho Image data such as shown from Camera 0 and from Camera 1 in FIGS. 17A and 17B. An Orthographic Scan 0 provides camera 0 Pixel Intensity data 182 at coordinates x and y (Pixel (OS0, x,y)). Likewise an Orthographic Scan 1 provides camera 0 Pixel Intensity data 183 at coordinates x and y (Pixel (OS1, x,y)). The pixels are compared at compare module 184, and a value from the pixels (for example, the least intense value pixel, in a Minimum finder 185, would eliminate specular reflection from one camera in favor of a diffuse reflection intensity value from the other camera) is selected for assembly of the Enhanced Image 186. The Ortho Scan 0 data loop 187 and the Ortho Scan 1 data loop 188 repeat the process for successive pixels, and so on.

Figure 19A:
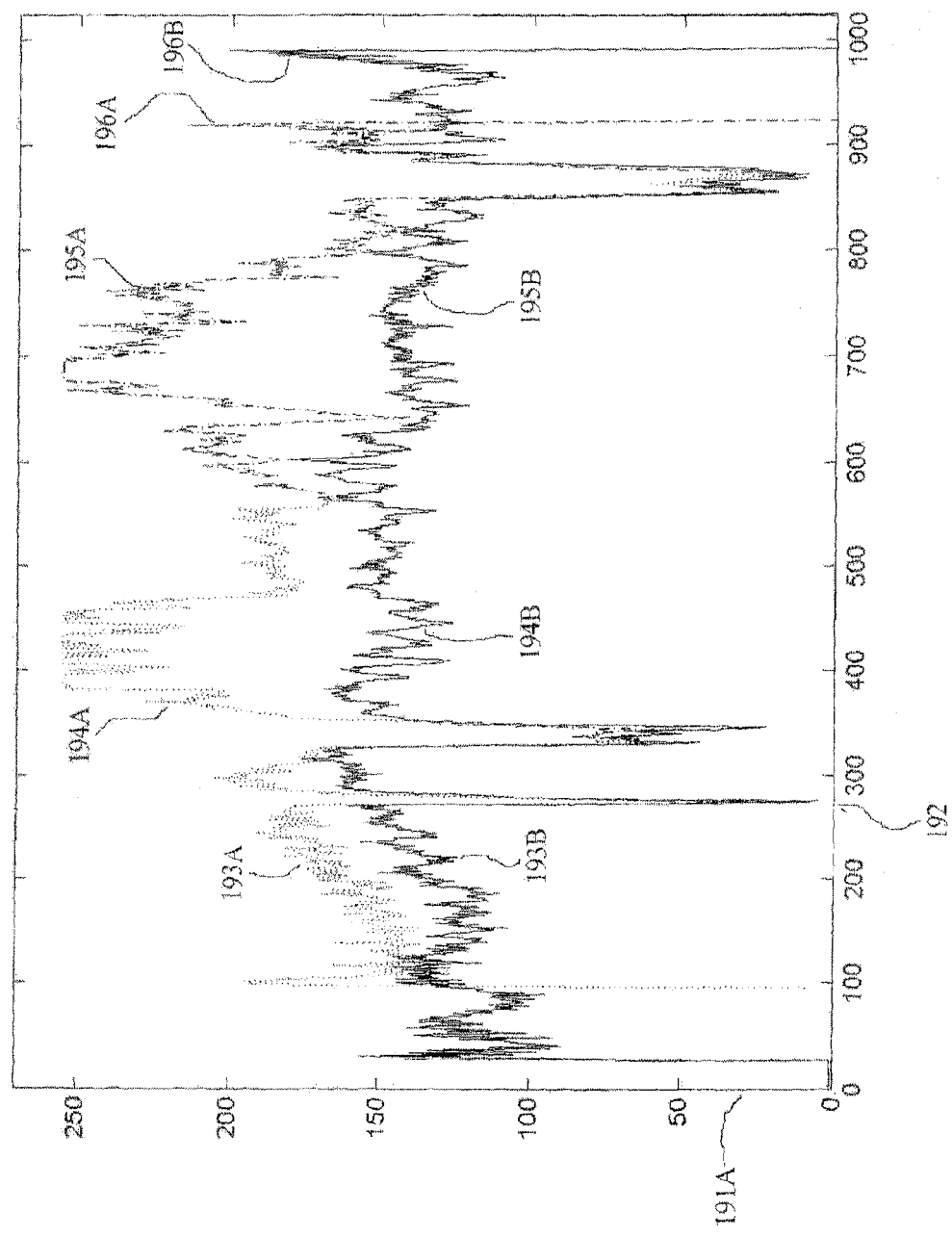
FIG. 19A is a graph of three lines of Image output data, one from Ortho Image 0, one from Ortho Image 1, and a line of Enhanced Image data generated by selectively combining data from Ortho Image 0 and Ortho Image 1.
Figure 19B:
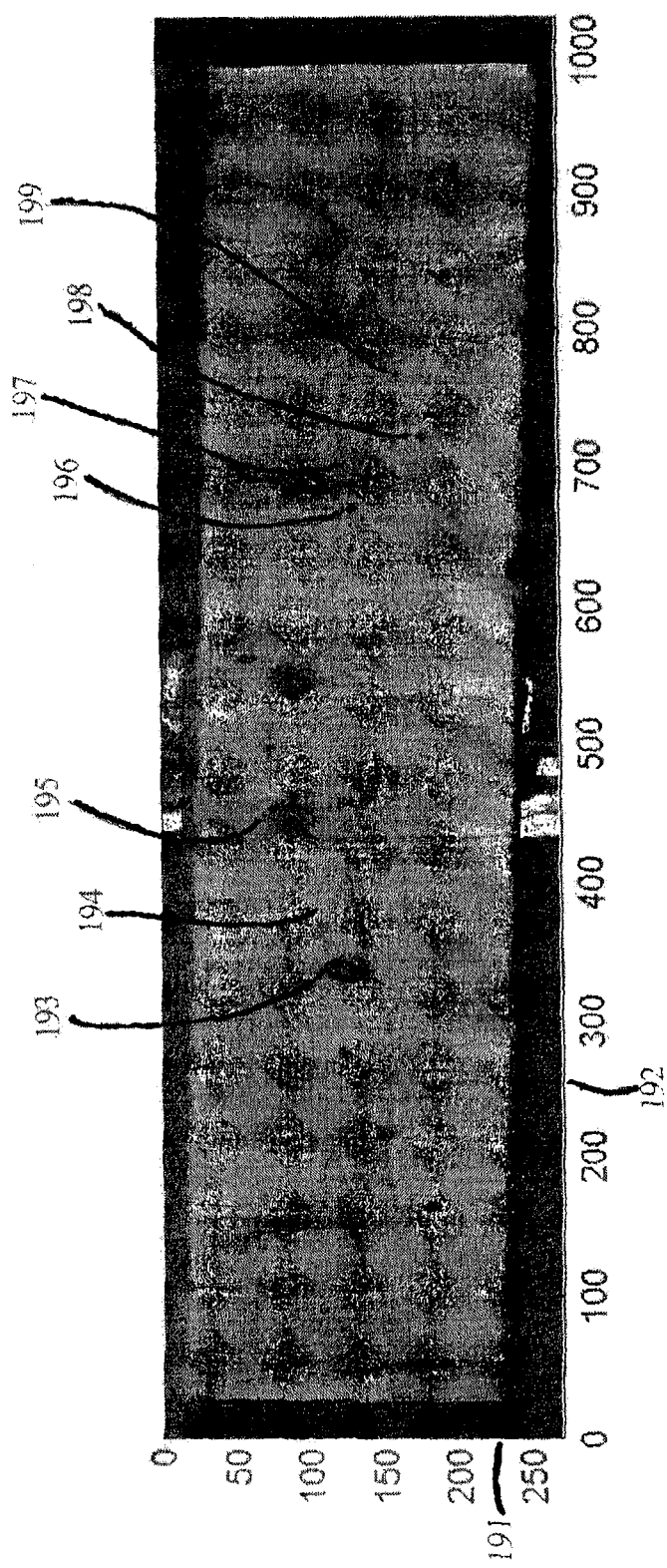
FIG. 19B is an actual Enhanced Image formed from Raw Image data with the method and apparatus of the present invention.

FIG. 19A shows three intensity lines of data from a scan line across the board shown in FIGS. 16A, 16B, 17A, 17B and 19B: a Camera 0 Ortho 0 data line, which has areas of overly intense image data at, for example, 193A and 194A, a Camera 1 Ortho 1 data line, which likewise has overly intense image data in different pixel locations, for example at 195A and 196A, and an Enhanced Image data line 194B which has been selected pixel by pixel from the other two lines by the method of FIG. 18, yielding, for example, point 193B from the Camera 1 Ortho 1 data line (rather than the data at 193A from Camera 0 Ortho 0) and point 195B from the Camera 0 Ortho 0 data line (rather than the data at 195A from Camera 1 Ortho 1). Areas of high image data intensity such as 196B on the Enhanced Image data line reflect an actual anomaly, in this case an edge on the board. The area (approximately from pixel 930 to pixel 990) between the vertical line below 196A and the vertical line below 196B has only one data line—only one camera provides data here due to parallax. Likewise there is only a single data line (from the other camera) on the extreme left in FIG. 19A up to about pixel 95. The scan window in which the invention method is valid is where the data from both the first and second camera overlap, for example, pixel 128 to pixel 896 along pixel number axis 192. It is convenient to reduce the operable scan window to known increments such as plus and minus 12 inches of target width from a center line below the center of the scan head—this would be from pixel 128 to 896 in FIG. 19B, along pixel number axis 192, In FIG. 19A, the vertical axis 191A is Flattened and Gridized Intensity. The horizontal-axis is Gridized pixel number across the scan line depicted for the two Ortho data lines and the resultant Enhanced data line. An array of such Enhanced Image data lines can be assembled into complete Enhanced Images such as is shown in FIG. 19B.

FIG. 19B shows an actual Enhanced Image from the method and apparatus of the invention. The vertical scan number axis 191 and the horizontal pixel number axis 192 relate to the scan respective number axis and horizontal axis in each of FIGS. 16A, 16B, 17A, and 17B, They do not correspond on a linear basis, however, because the parallax has been removed in the process from FIGS. 16A and 16B through to the Enhanced Image of FIG. 19B. That image is of the same actual board as was imaged differently in FIGS. 16A, 16B, 17A, and 17B. In the Enhanced Image of FIG. 19B, the specular reflection of the earlier images is eliminated. The selected features (large knots 193 and 195, and small knots 196, 198, 199) are not only clear but are now accurately sized. The former areas of specular reflection at 194 and 197 respectively have been eliminated. Even the wood grain in both those areas can now be accurately read by a machine. To summarize, the final Enhanced Image in FIG. 19B is void of specular reflections, is compensated for variations in illumination radiation pattern and camera sensitivities, and its surface features (knots, grain patterns) as represented are geometrically correct with respect to the actual target object.

Figure 20:
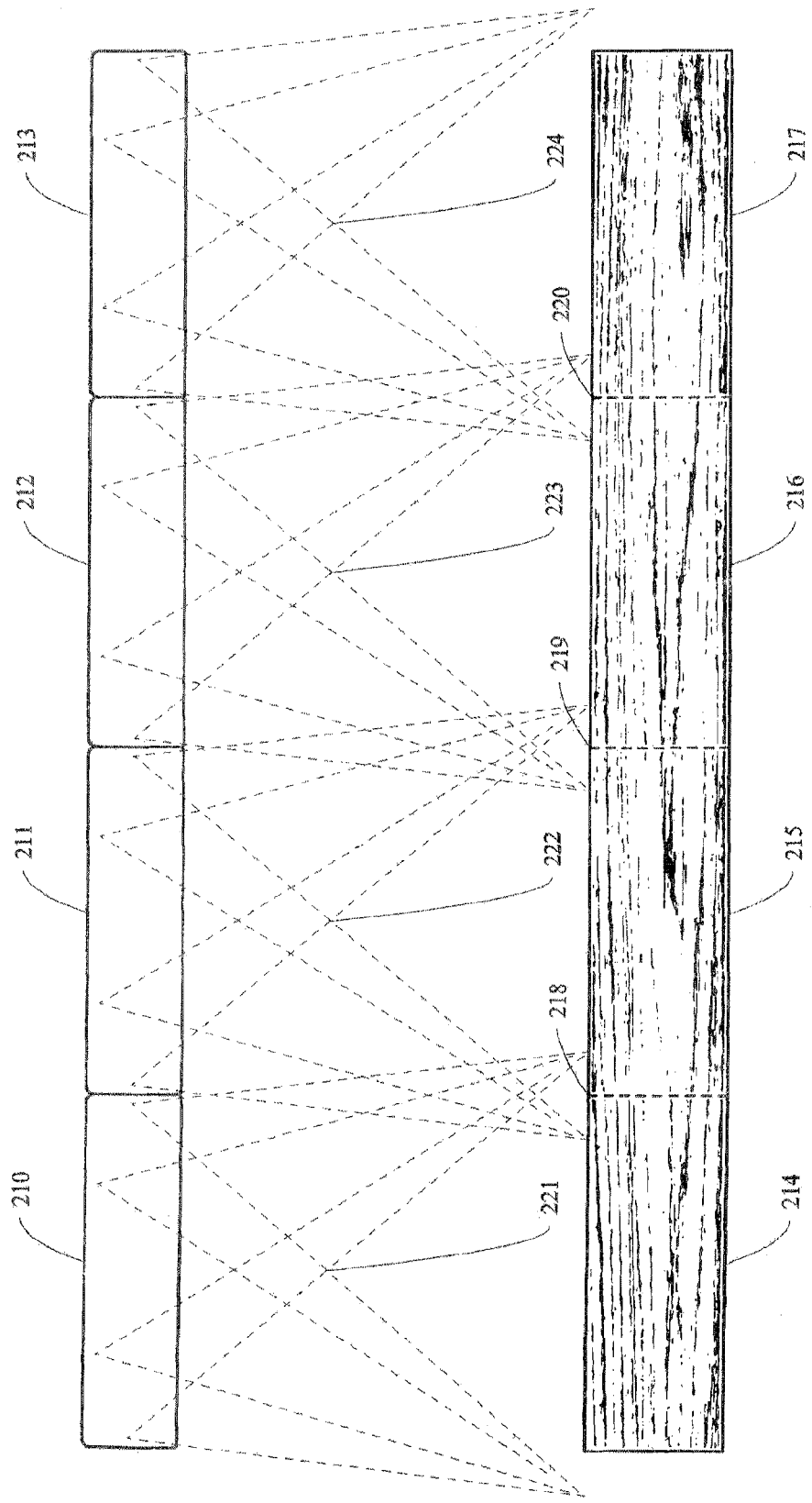
FIG. 20 is a schematic representation of a series of four scan heads, scanning four respective overlapping segments of a long board.

Referring to FIG. 20, it will be seen that multiple scan heads 210, 211, 212, and 213 can be positioned over a long length of lumber consisting of board scan segments 214, 215, 216, and 217. The fields of illumination and cameras' view 221, 222, 223, and 224 from the respective scan heads should overlap the board scan segments. This will enable multiplexing of the scan head so that overlapping scans can be done by adjacent scan heads around the board scan segment lines 218, 219, and 200. Preferred pixel values can then be selected for the lines between board scan segments, in the same manner as described above, rather than needlessly dealing with un-enhanced image data as stitch lines. The dotted lines between the board scan segments 214, 215, 216 and 217 are shown for explanatory purposes but in practice the corresponding stitch lines are rendered essentially invisible by the application of the Enhanced Imaging method and apparatus herein disclosed.

The control and timing of sequential flashing of different illuminators to record the same target object locations on a pixel-by-pixel and line-by-line bases works well if the time between flashes is of sufficiently short duration that the relevant sequential illuminations are effectively simultaneous having respect to the timing and resolution limits of the equipment. For example, if 40 inches of target board surface pass under the scanner head every second, and 1000 scans per second are taken with a coded laser alternating with 1000 scans per second taken with an LED array and first and second color cameras, during a pair of alternate scans (½ a millisecond between scans) the board has only traveled about 0.020 of an inch during the pair of alternate scans, which is well within computational limits for correlating to pixel resolution—effectively the process works as well as if the scan were taken with the target not moving at each scan, and then advanced between scans and is analogous to moving events appearing to be frozen during strobe light illumination. Whether or not both monochrome and color illumination and camera apparatus are used, the Enhanced Image of the present invention is made from combining data from single scans by two different cameras that have received light reflected by the target surface from at least one illuminator.

The enhanced, accurate imaging method of the present invention may be applied with:
  a) two or more cameras that are sensitized to the illuminator's output and are viewing the same area on the target;
  b) multiple special target illuminators and correspondingly sensitized multiple cameras;
  c) a multiplicity of area cameras and ambient lighting;
with multiple parallel stages (two of which are illustrated in FIG. 1) for the image data from each camera accordingly used before the Selective combining. Additional orthographic image data from at least one additional camera (over Camera 0 and Camera 1) can be compared with first camera orthographic image data and second camera orthographic data for a coordinate position on the target object, and a value of the orthographic image data for a particular coordinate position on the target object can be selected based on a pre-selected criteria for use of first, second, and additional orthographic data in assembling an enhanced image.

Additionally, the method and apparatus of the present invention can be applied to the imaging of an object's internal interfaces (e.g. of laminate material), when suitable penetrating radiation is reflected from such internal interfaces and detectable (as reflected) by a suitable receiver.

The system may optionally provide Enhanced Images that are additionally enhanced in detail by using different cameras having different appropriate focal lengths or different wavelength sensitivities. The system can yield improved results if successive Red, Green and Blue scans are taken quickly enough to be effectively simultaneous within the limits of resolution of the equipment. The RGB scans can be compared, and Red, Green or Blue pixels can be discarded if they are unusual when compared with the corresponding pixel of the other two colors. Small images errors due to vibrations and slight misalignment of the equipment as the scanning proceeds can be eliminated by this method. Varying exposure times as between the first and second cameras is also possible with this invention, because the pixels recorded by each camera are identifiable and mappable on a one-to-one basis, that is, they can be matched in time and space, and compared, in order to select the more informative or more useful pixel data value. The invention enables the comparing of different perspective images of a moving object on a corresponding pixel by pixel basis and coalescing a new image from the two sets of pixel data that draws on the more informative or more useful pixels from each set.

In the Selective combining method described above, the lowest intensity pixel level was selected from each of the two Ortho Images to render an Enhanced Image absent of specular reflection. Just as both Ortho images are comparable with the present method and apparatus, both on a pixel by pixel basis and on a responsiveness basis, other image selection criterion may be applied to this method. Possible other selection criteria include, but are not limited to: pixel intensity, absence or presence of specular reflection, specific color intensity level in a multi-color image, local variation in intensity, focus or any other criteria which is deterministic within the sets of image data. Focus, for example, can be quantified based on the magnitude of first differences, said first differences being in one or both dimensions within the image.

Higher dynamic range may be achieved by using the method and apparatus of the present invention and controlling the exposure time of one of the cameras with respect to the other camera. For example, if Camera 0 has an exposure time of 10 mSec., and Camera 1 has an exposure time of $^{10}/_{64}$ mSec., the orthographic images can be combined to increase pixel depth in the Enhanced image by a factor of 64 (6 bits).

Variants within the scope of the invention will be apparent to those skilled in the field of the invention. For example, the illumination source for the acquisition of the raw image data may be a laser, an LED, incandescent or any other light source or array of the same. The invention essentially provides a fast, versatile and effective way of generating accurate enhanced images based on multiple camera image data, with selective combining of the best portions of that data enabled by the apparatus set-up and the intermediate processing of the respective camera's image data with the steps disclosed above and as set out in the Claims hereto.

We claim:

1. A method for generating accurate, high quality images comprising the steps of: a) acquiring a first raw scan of a portion of a target object across a scan line in a scan zone with a first camera and simultaneously acquiring a second raw scan of the same portion of the target object across the scan line in the scan zone with a second camera, the second camera being separated from the first camera in a camera zone such that the first and second camera have substantially different perspectives of the same portion of the target object; b) converting the first raw scan from analog to digital format resulting in first raw image data and converting the second raw scan from analog to digital format resulting in second raw image data; c) processing the first raw image data with a first set of flattening coefficients derived from measurements of variations in illumination and in first camera response across the scan line to a uniform diffusely reflecting target in the scan zone, resulting in first flattened image data from the target object, and processing the second raw image data with a second set of flattening coefficients derived from measurements of variations in illumination and in second camera response across the scan line to the uniform diffusely reflecting target in the scan zone, resulting in second flattened image data from the target object; d) compensating for parallax in first flattened image data with a first set of calculations, resulting in first orthographic image data; and compensating for parallax in second flattened image data with a second set of calculations, resulting in second orthographic image data; e) comparing first orthographic image data corresponding to a coordinate location that is a prior known geometric profile location on the target object with second orthographic image data corresponding to the coordinate location; f) selecting a pixel intensity value, for use as enhanced image data representing the coordinate location on the target object, from one of: i) the first orthographic image data corresponding to the coordinate location ii) the second orthographic image data corresponding to the coordinate location; iii) a result of a formula using a combination of the first and second orthographic data corresponding to the coordinate location.

2. The method of claim 1, in which the steps of claim 1 are repeated with scanning of sequential scan lines across the target object, resulting in sequences of enhanced image data representing corresponding coordinate locations on the target object, and assembling an enhanced image of the target object from the sequences of enhanced image data.

3. The method of claim 2, in which movement of the target object during scanning is controlled to maintain a known image aspect ratio during scanning and to avoid distortion of the enhanced image.

4. The method of claim 3, in which an electronic signal from a z-axis position encoder is used during the scanning to indicate target object position relative to a reference position for the scan zone.

5. The method of claim 4, in which scans are triggered by the position encoder at known incremental intervals of a target object movement through the scan zone.

6. The method of claim 1, in which pixel intensity value selected for use as enhanced image data is a lower of two corresponding orthographic pixel data values from first orthographic data and from second orthographic data, thereby selecting lower specular reflection from the target object.

7. The method of claim 1, in which geometric positions of relevant portions of the target object are obtained by structured light geometric scanning, enabling mapping of first raw data pixels to corresponding second raw data pixels.

8. The method of claim 7, in which: an uncoded laser illuminator is used in conjunction with a monochrome camera to obtain at least one set of monochrome raw image data.

9. The method of claim 7, in which an LED illuminator is used in conjunction with a color camera to obtain at least one set of raw image data.

10. The method of claim 7, in which alternate firing from a structured light geometric scanning illuminator to obtain target object position data, and from a raw image data illuminator is effectively simultaneous with respect to scanning movement of the target object by having a time between flashes from the respective illuminators sufficiently short that a computed adjustment of coordinate positions to compensate for scanning movement of the target object between firings is within computational limits for correlating resulting structured light geometric scanning data and corresponding raw image data to pixel resolution.

11. The method of claim 1, in which two dimensional enhanced images are generated by combining a successive number of linear scans of a surface.

12. The method of claim 1, in which: a) processing of the first raw image data with the first set of flattening coefficients derived from measurements of variations in illumination and in first camera response across the scan line to the uniform diffusely reflecting target in the scan zone, resulting in first flattened image data from the target object, and b) processing the second raw image data with the second set of flattening coefficients derived from measurements of variations in illumination and in second camera response across the scan line to the uniform diffusely reflecting target in the scan zone, resulting in second flattened image data from the target object, are performed to a standard level of image flattening with multiple identical adjacent scan heads each using a respective illuminator, a first respective camera and a second respective camera, and the processing method of claim 1; and multiple flattened images of adjacent areas on the target below adjacent scan heads obtained by such processing are joined to form an overall image of the target without discontinuity of image accuracy between multiple flattened images from respective adjacent scan heads.

13. The method of claim 1, in which multiple images of adjacent areas on the target object are joined together along a geometrically exact pixel stitch line, in order to minimize discontinuity of target object features and discontinuity of image intensity values for adjacent geometric locations on the target object to below image background noise values.

14. The method of claim 1, in which a geometric profile of the target is derived using a structured light geometric scanner, and an LED is used to illuminate the target object for the first and second cameras during an image capture scan.

15. The method of claim 1, in which additional orthographic image data from at least one additional camera is compared with first camera orthographic image data and second camera orthographic data for a coordinate position on the target object, and a value of the orthographic image data for a particular coordinate position on the target object is selected based on a pre-selected criteria for use of first, second, and additional orthographic data in assembling an enhanced image.

16. The method of claim 2, in which: a) movement of the target object during scanning is controlled and measured to maintain a known image aspect ratio during scanning and to avoid distortion of the enhanced image; b) an electronic signal from a z-axis position encoder is used during the scanning to indicate target object position relative to a reference position for the scan zone; c) scans are triggered by the position encoder at known incremental intervals of a target object movement through the scan zone; d) pixel intensity value selected for use as enhanced image data is a lower of two corresponding orthographic pixel data values from first orthographic data and from second orthographic data, thereby selecting lower specular reflection from the target object.

17. The method of claim 2, in which: a) geometric positions of relevant portions of the target object are obtained by structured light geometric scanning, enabling mapping of first raw data pixels to corresponding second raw data pixels; b) alternate firing from a structured light geometric scanning illuminator to obtain target object position data, and from a raw image data illuminator is effectively simultaneous with respect to scanning movement of the target object by having a time between flashes from the respective illuminators sufficiently short that a computed adjustment of coordinate positions to compensate for scanning movement of the target object between firings is within computational limits for correlating resulting structured light geometric scanning data and corresponding raw image data to pixel resolution.

18. The method of claim 2, 16, or 17, in which two dimensional enhanced images are generated by combining a successive number of linear scans of a surface.

19. The method of claim 2, 16, or 17, in which: i) processing of the first raw image data with the first set of flattening coefficients derived from measurements of variations in illumination and in first camera response across the scan line to the uniform diffusely reflecting target in the scan zone, resulting in first flattened image data from the target object, and ii) processing the second raw image data with the second set of flattening coefficients derived from measurements of variations in illumination and in second camera response across the scan line to the uniform diffusely reflecting target in the scan zone, resulting in second flattened image data from the target object, are performed to a standard level of image flattening with multiple identical adjacent scan heads each using a respective illuminator, a first respective camera and a second respective camera, and the processing method of claim 1; and b) multiple flattened images of adjacent areas on the target below adjacent scan heads obtained by such processing are joined to form an overall image of the target, in which multiple images of adjacent areas on the target object are joined together along a geometrically exact pixel stitch line, in order to minimize discontinuity of target object features and discontinuity of image intensity values for adjacent geometric locations on the target object to below image background noise values.

20. The method of claim 2, 16, or 17 in which a geometric profile of the target is derived using coded light from a laser, and an LED is used to illuminate the target object for the first and second cameras during an image capture scan.

21. Apparatus for generating accurate, high quality images comprising: a) at least two cameras, including a first camera set up for acquiring a first raw scan of a portion of a target object across a scan line in a scan zone with a first camera and simultaneously acquiring a second raw scan of the same portion of the target object across the scan line in the scan zone with a second camera, the second camera being separated from the first camera in a camera zone such that the first and second camera have substantially different perspectives of the same portion of the target object; b) an analog to digital converter set up for converting the first raw scan from analog to digital format resulting in first raw image data and converting the second raw scan from analog to digital format resulting in second raw image data; c) a flattening image processing module that processes the first raw image data with a first set of flattening coefficients derived from measurements of variations in illumination and in first camera response across the scan line to a uniform diffusely reflecting target in the scan zone, resulting in first flattened image data from the target object, and that processes the second raw image data with a second set of flattening coefficients derived from measurements of variations in illumination and in second camera response across the scan line to the uniform diffusely reflecting target in the scan zone, resulting in second flattened image data from the target object; d) a gridizing image processing module that compensates for parallax in first flattened image data with a first set of calculations, resulting in first orthographic image data, and compensates for parallax in second flattened image data with a second set of calculations, resulting in second orthographic image data; e) a selective combining image processing module that compares first orthographic image data corresponding to a coordinate location that is a prior known geometric profile location on the target object with second orthographic image data corresponding to the coordinate location; and selects a pixel intensity value, for use as enhanced image data representing the coordinate location on the target object, from one of: i) the first orthographic image data corresponding to the coordinate location; ii) the second orthographic image data corresponding to the coordinate location; iii) a result of a formula using a combination of the first and second orthographic data corresponding to the coordinate location.

22. The apparatus of claim 21, further comprising a computer set up to obtain sequential scan lines across the target object and sequences of enhanced image data representing corresponding coordinate locations on the target object, and to assemble an enhanced image of the target object from the sequences of enhanced image data.

23. The apparatus of claim 21, further comprising a position encoder set up to track movement of the target object during scanning in order to maintain a known image aspect ratio during scanning and to avoid distortion of the enhanced image.

24. The apparatus of claim 23, in which the position encoder outputs an electronic signal during scanning to indicate target object position along a z-axis relative to a reference position for the scan zone.

25. The apparatus of claim 23, in which the position encoder triggers scans at known incremental intervals of a target object movement through the scan zone.

26. The apparatus of claim 21, in which the selective combining image processing module selects for use as enhanced image data a lower of two corresponding orthographic pixel data values from first orthographic data and from second orthographic data, thereby selecting lower specular reflection from the target object.

27. The apparatus of claim 21, further comprising a structured light geometric scanner for obtaining geometric positions of relevant portions of the target object, to enabling mapping of first raw data pixels to corresponding second raw data pixels.

28. The apparatus of claim 21, in which an uncoded laser illuminator is used in conjunction with a monochrome camera to obtain at least one set of monochrome raw image data.

29. The apparatus of claim 21, in which in which an LED illuminator is used in conjunction with a color camera to obtain at least one set of raw image data.

30. The apparatus of claim 21, in which a structured light geometric scanner to obtain target object position data, is set up to fire alternately but effectively simultaneously with a raw image data illuminator with respect to scanning movement of the target object, by being set up to have a time between flashes from the respective illuminators sufficiently short that a computed adjustment of coordinate positions to compensate for scanning movement of the target object between firings is within computational limits for correlating resulting coded laser geometric data and corresponding raw image data to pixel resolution.

31. The apparatus of claim 21, further comprising a computer that generates two dimensional enhanced images by combining a successive number of linear scans of a surface.

32. The apparatus of claim 21, further comprising a computer that: a) processes the first raw image data with the first set of flattening coefficients derived from measurements of variations in illumination and in first camera response across the scan line to the uniform diffusely reflecting target in the scan zone, resulting in first flattened image data from the target object, and b) processes the second raw image data with the second set of flattening coefficients derived from measurements of variations in illumination and in second camera response across the scan line to the uniform diffusely reflecting target in the scan zone, resulting in second flattened image data from the target object; to a standard level of image flattening, and coordinates multiple identical adjacent scan heads each using the apparatus of claim 21, and resulting multiple flattened images of adjacent areas on the target below adjacent scan heads obtained by such processing, to form an overall image of the target without discontinuity of image accuracy between multiple flattened images from respective adjacent scan heads.

33. The apparatus of claim 21, in which a computer joins multiple images of adjacent areas on the target object along a pixel stitch line, to render discontinuity of target object features and discontinuity of image intensity values for adjacent geometric locations on the target object below background noise values.

34. The apparatus of claim 21, in which a structured light geometric scanner obtains a geometric profile of the target object, and an LED illuminator is used to illuminate the target object for the first and second cameras during an image capture scan.

35. The apparatus of claim 21, in which a computer is set up to compare additional orthographic image data from at least one additional camera with first camera orthographic image data and second camera orthographic data for a coordinate position on the target object, and the computer selects a value of the orthographic image data for a particular coordinate position on the target object based on a pre-selected criteria for use of first, second, and additional orthographic data in assembling an enhanced image.

36. The apparatus of claim 22, further comprising a position encoder set up to track movement of the target object during scanning in order to maintain a known image aspect ratio during scanning and to avoid distortion of the enhanced image, in which the position encoder outputs an electronic signal during scanning to indicate target object position along a z-axis relative to a reference position for the scan zone, and the position encoder triggers scans at known incremental intervals of a target object movement through the scan zone.

37. The apparatus of claim 21, further comprising: a) a structured light geometric scanner illuminator for obtaining geometric positions of relevant portions of the target object, to enabling mapping of first raw data pixels to corresponding second raw data pixels; b) the structured light geometric scanner illuminator is set up to fire alternately but effectively simultaneously with a raw image data illuminator with respect to scanning movement of the target object, by being set up to have a time between flashes from the respective illuminators sufficiently short that a computed adjustment of coordinate positions to compensate for scanning movement of the target object between firings is within computational limits for correlating resulting geometric data and corresponding raw image data to pixel resolution.

38. The apparatus of claim 22, 36, or 37, in which the computer generates two dimensional enhanced images by combining a successive number of linear scans of a surface.

39. The apparatus of claim 22, 36, or 37 is part of an aligned multiplicity of such apparatus, in which an aligned multiplicity computer: a) processes the first raw image data with the first set of flattening coefficients derived from measurements of variations in illumination and in first camera response across the scan line to the uniform diffusely reflecting target in the scan zone, resulting in first flattened image data from the target object, and b) processes the second raw image data with the second set of flattening coefficients derived from measurements of variations in illumination and in second camera response across the scan line to the uniform diffusely reflecting target in the scan zone, resulting in second flattened image data from the target object; to a standard level of image flattening, and coordinates multiple identical adjacent scan heads each using the apparatus of claim 21, and resulting multiple flattened images of adjacent areas on the target below adjacent scan heads obtained by such processing, to form an overall image of the target without discontinuity of image accuracy between multiple flattened images from respective adjacent scan heads; and joins multiple images of adjacent areas on the target object along a geometrically exact pixel stitch line, to render discontinuity of target object features and discontinuity of image intensity values for adjacent geometric locations on the target object below background noise values.

40. The apparatus of claim 22, 36 or 37, in which a laser provides coded light to obtain a geometric profile of the target object, and an LED illuminator is used to illuminate the target object for the first and second cameras during an image capture scan.

* * * * *